(12) United States Patent
Rebellino et al.

(10) Patent No.: US 11,090,033 B2
(45) Date of Patent: Aug. 17, 2021

(54) MRI GUIDED BIOPSY DEVICE WITH ROTATING DEPTH STOP DEVICE

(71) Applicant: Devicor Medical Products, Inc., Cincinnati, OH (US)

(72) Inventors: Jordan Rebellino, Cincinnati, OH (US); John Kevin Bruce, Burlington, KY (US)

(73) Assignee: Devicor Medical Products, Inc., Cincinnati, OH (US)

( * ) Notice: Subject to any disclaimer, the term of this patent is extended or adjusted under 35 U.S.C. 154(b) by 321 days.

(21) Appl. No.: 16/137,072

(22) Filed: Sep. 20, 2018

(65) Prior Publication Data

US 2019/0083071 A1   Mar. 21, 2019

Related U.S. Application Data

(60) Provisional application No. 62/560,771, filed on Sep. 20, 2017.

(51) Int. Cl.
| *A61B 90/10* | (2016.01) |
| *A61B 17/34* | (2006.01) |
| *A61B 10/02* | (2006.01) |
| *A61B 10/00* | (2006.01) |
| *A61B 90/11* | (2016.01) |
| *A61B 5/055* | (2006.01) |
| *A61B 90/00* | (2016.01) |

(52) U.S. Cl.
CPC ...... *A61B 10/0275* (2013.01); *A61B 10/0041* (2013.01); *A61B 10/0283* (2013.01);
(Continued)

(58) Field of Classification Search
CPC ............ A61B 17/3403; A61B 10/0233; A61B 10/0266; A61B 10/0275; A61B 10/0041;
(Continued)

(56) References Cited

U.S. PATENT DOCUMENTS 5,217,438 A   6/1993   Davis et al.
5,526,822 A   6/1996   Burbank et al.
(Continued)

FOREIGN PATENT DOCUMENTS

WO   WO 2016/201083 A1   12/2016

OTHER PUBLICATIONS

International Search Report and Written Opinion dated Jan. 18, 2019 for Application No. PCT/US2018/052004, 11 pgs.
U.S. Appl. No. 62/560,771, filed Sep. 20, 2017.

*Primary Examiner* — David J. McCrosky
(74) *Attorney, Agent, or Firm* — Frost Brown Todd LLC

(57) ABSTRACT

A bi-directional depth stop for use with biopsy instrument including a body and a pair of blades. The body defines a channel sized to receive a cannula associated with the biopsy instrument. The channel includes a first pair of opposing concave surfaces and a second pair of opposing concave surfaces. The first pair and second pair of opposing concave surfaces together form a superimposed bi-oval-shaped cross-section. Each blade of the pair of blades projects inwardly into a concave surface of the first pair of opposing concave surfaces such the pair of blades are disposed on an opposing side of the body. In some instances, the concave surfaces may be beneficial to provide rotation of the dept stop in two directions rather than a single direction.

19 Claims, 15 Drawing Sheets

(52) U.S. Cl.
CPC ...... *A61B 17/3403* (2013.01); *A61B 17/3421* (2013.01); *A61B 90/10* (2016.02); *A61B 90/11* (2016.02); *A61B 5/055* (2013.01); *A61B 17/3494* (2013.01); *A61B 2010/0208* (2013.01); *A61B 2017/3405* (2013.01); *A61B 2017/3411* (2013.01); *A61B 2090/034* (2016.02); *A61B 2090/062* (2016.02); *A61B 2090/0811* (2016.02); *A61B 2090/374* (2016.02); *A61B 2217/005* (2013.01)

(58) Field of Classification Search
CPC ........ A61B 90/11; A61B 90/17; A61B 90/10; A61B 10/0283; A61B 17/3421; A61B 2090/0811; A61B 2090/062; A61B 17/3494; A61B 2090/034; A61B 2017/3411; A61B 2217/005; A61B 2017/3405; A61B 2010/0208; A61B 5/055; A61B 2090/374
See application file for complete search history.

(56) References Cited

U.S. PATENT DOCUMENTS

| | | |
|---|---|---|
| 5,954,670 A | 9/1999 | Baker |
| 6,086,544 A | 4/2000 | Hibner et al. |
| 6,626,849 B2 | 9/2003 | Huitema et al. |
| 6,752,768 B2 | 6/2004 | Burdorff et al. |
| 7,442,171 B2 | 10/2008 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,277,394 B2 | 10/2012 | Hibner |
| 8,328,732 B2 | 12/2012 | Parihar et al. |
| 8,568,333 B2 | 10/2013 | Hibner et al. |
| 8,702,623 B2 | 4/2014 | Parihar et al. |
| 8,764,680 B2 | 7/2014 | Rhad et al. |
| 8,858,465 B2 | 10/2014 | Fiebig |
| 9,486,186 B2 | 11/2016 | Fiebig et al. |
| 9,931,104 B2 | 4/2018 | Rhad et al. |
| 9,999,406 B2 | 6/2018 | Hibner et al. |
| 10,064,607 B2 | 9/2018 | Keller et al. |
| 10,123,820 B2 | 11/2018 | Hibner et al. |
| 10,201,333 B2 | 2/2019 | Nock et al. |
| 2010/0160819 A1 | 6/2010 | Parihar et al. |
| 2013/0324882 A1 | 12/2013 | Mescher |
| 2014/0039343 A1 | 2/2014 | Mescher et al. |
| 2014/0039345 A1* | 2/2014 | Hibner ............... A61B 17/3403 600/567 |
| 2017/0311932 A1 | 11/2017 | Rebellino |

* cited by examiner

MRI GUIDED BIOPSY DEVICE WITH ROTATING DEPTH STOP DEVICE

PRIORITY

This application claims priority to U.S. Provisional Patent App. No. 62/560,771 entitled "MRI Guided Biopsy Device with Rotating Depth Stop Device," filed Sep. 20, 2017, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 11, 2003; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; and U.S. Pat. No. 8,858,465, entitled "Biopsy Device with Motorized Needle Firing," issued Oct. 14, 2014. The disclosure of each of the above-cited U.S. Patents is incorporated by reference herein.

Additional exemplary biopsy devices and biopsy system components are disclosed in U.S. Pat. Pub. No. 2010/0113973, entitled "Biopsy Device with Rotatable Tissue Sample Holder," published May 6, 2010, issued as U.S. Pat. No. 8,241,226 on Aug. 14, 2012; U.S. Pat. Pub. No. 2010/0160819, entitled "Biopsy Device with Central Thumbwheel," published Jun. 24, 2010, now abandoned; U.S. Pat. Pub. No. 2010/0317997, entitled "Tetherless Biopsy Device with Reusable Portion," published Dec. 16, 2010, issued as U.S. Pat. No. 8,206,316 on Jun. 26, 2012; U.S. Pat. Pub. No. 2012/0109007, entitled "Handheld Biopsy Device with Needle Firing," published May 3, 2012, issued as U.S. Pat. No. 8,764,680 on Jul. 1, 2014; and U.S. Pat. Pub. No. 2013/0324882, entitled "Control for Biopsy Device," published Dec. 5, 2013, now abandoned. The disclosure of each of the above-cited U.S. Patent Application Publications, U.S. Non-Provisional Patent Applications, and U.S. Provisional Patent Applications is incorporated by reference herein.

In U.S. Pat. Pub. No. 2007/0255168, entitled "Grid and Rotatable Cube Guide Localization Fixture for Biopsy Device" published Nov. 1, 2007, issued as U. S. Pat. No. 8,568,333 on Oct. 29, 2013, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
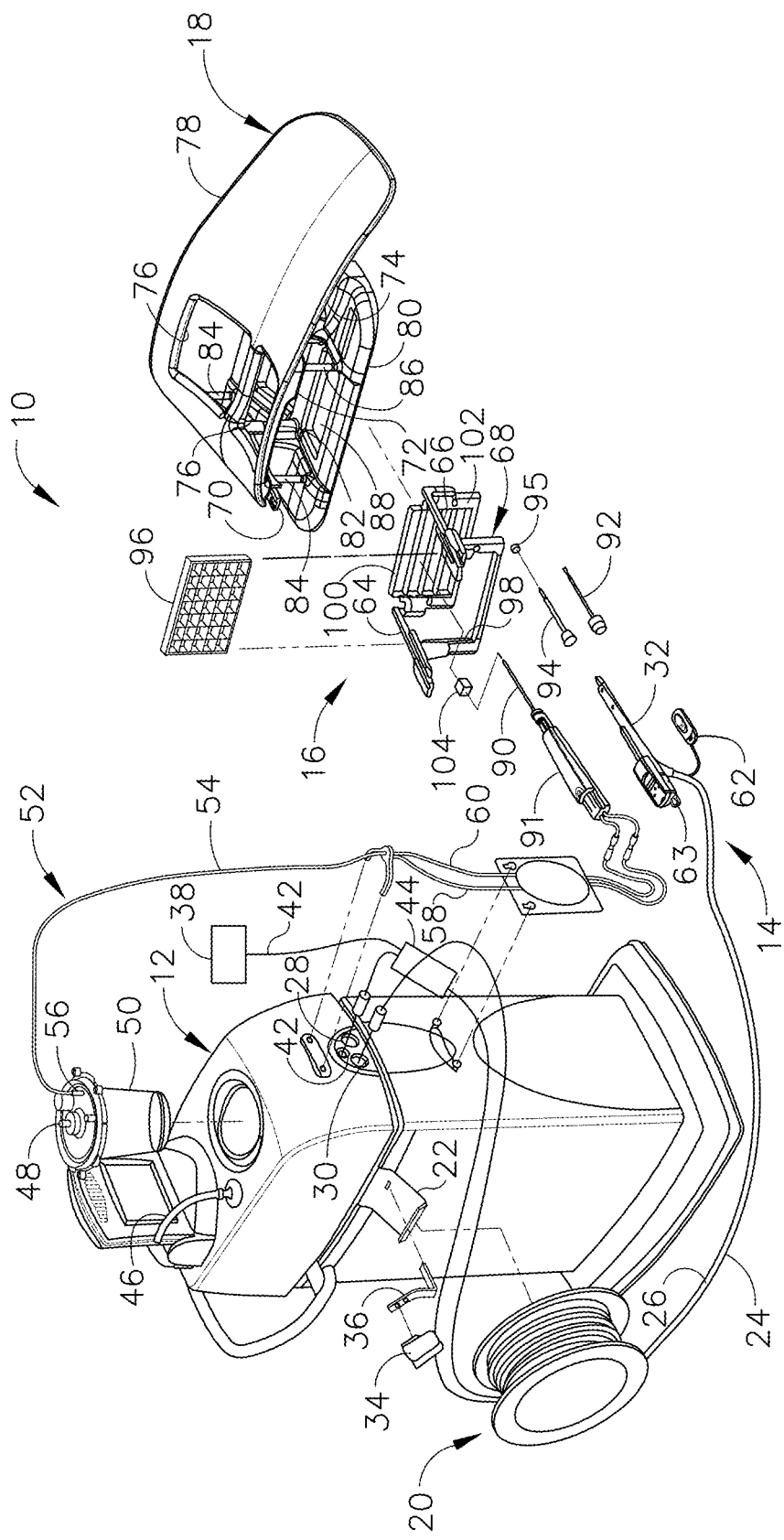
FIG. 1 depicts a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary MRI Biopsy Control Module

Figure 2:
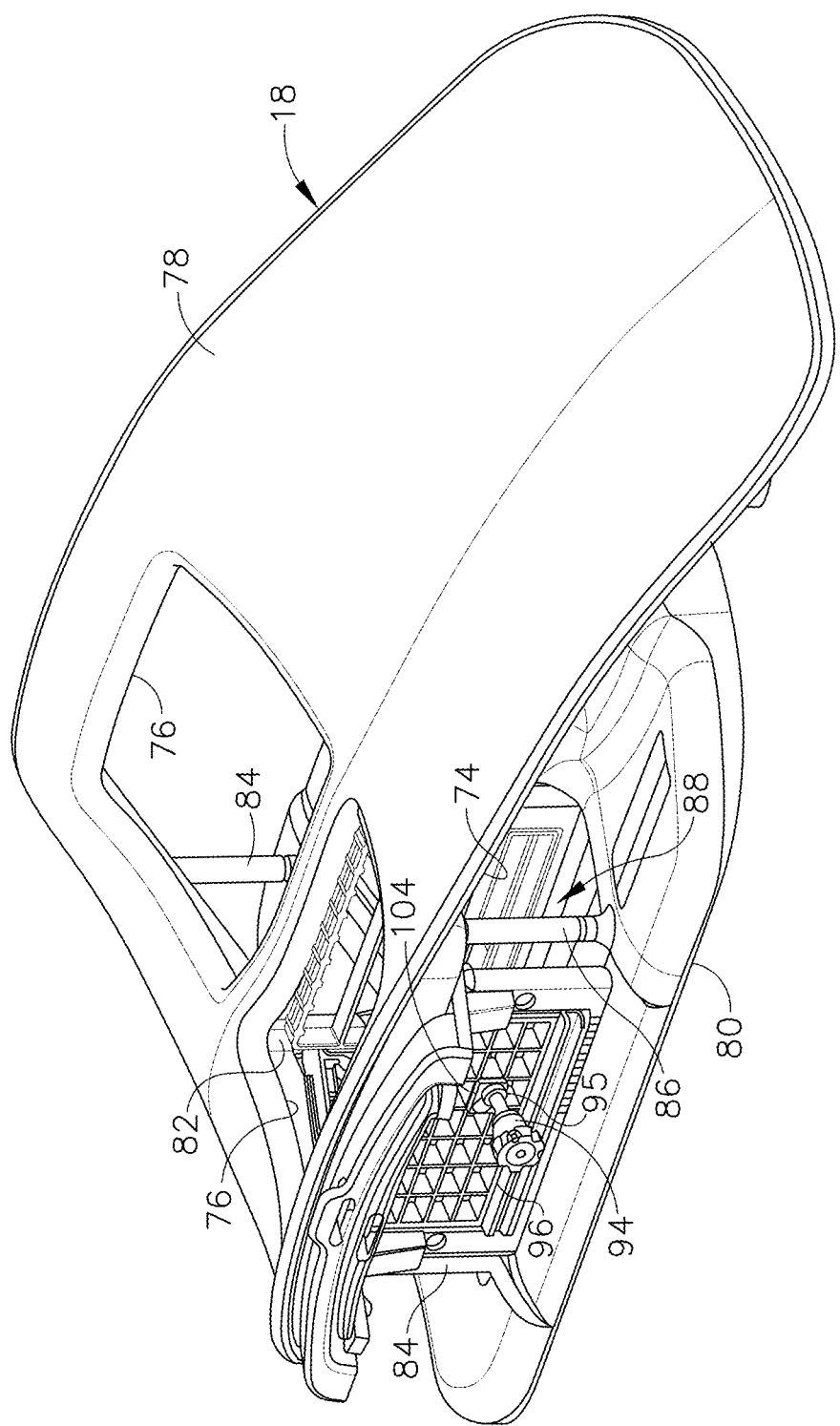
FIG. 2 depicts a perspective view of a breast coil receiving the localization fixture of FIG. 1.
Figure 3:
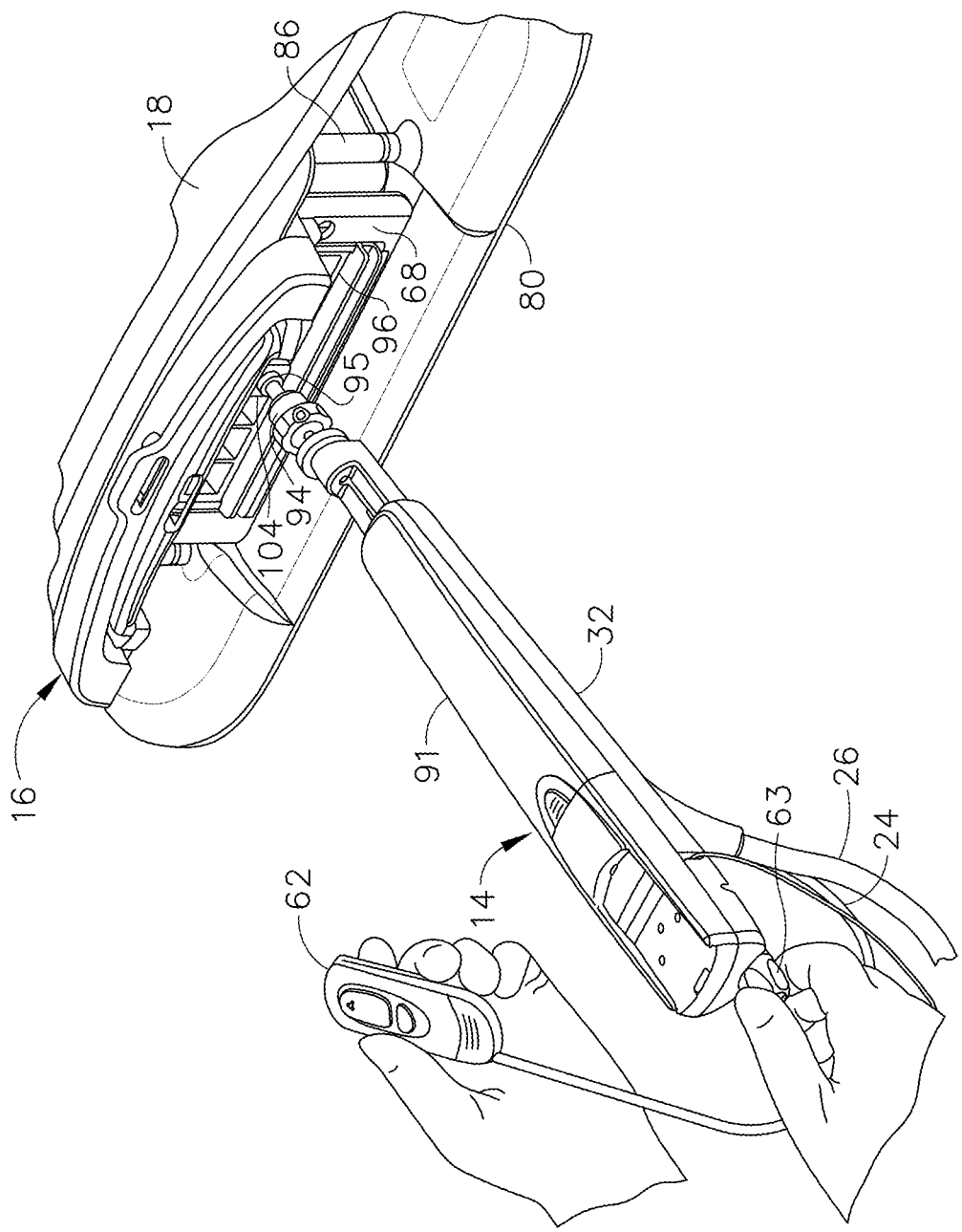
FIG. 3 depicts a perspective view of the biopsy device inserted through the rotatable cube within the cube plate of the localization fixture attached to the breast coil of FIG. 2.

In FIGS. 1-3, an MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. Pat. No. 8,328,732, entitled "Control Module Interface for MRI Biopsy Device," issued Dec. 11, 2012, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Exemplary Localization Assembly

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Exemplary Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 7:
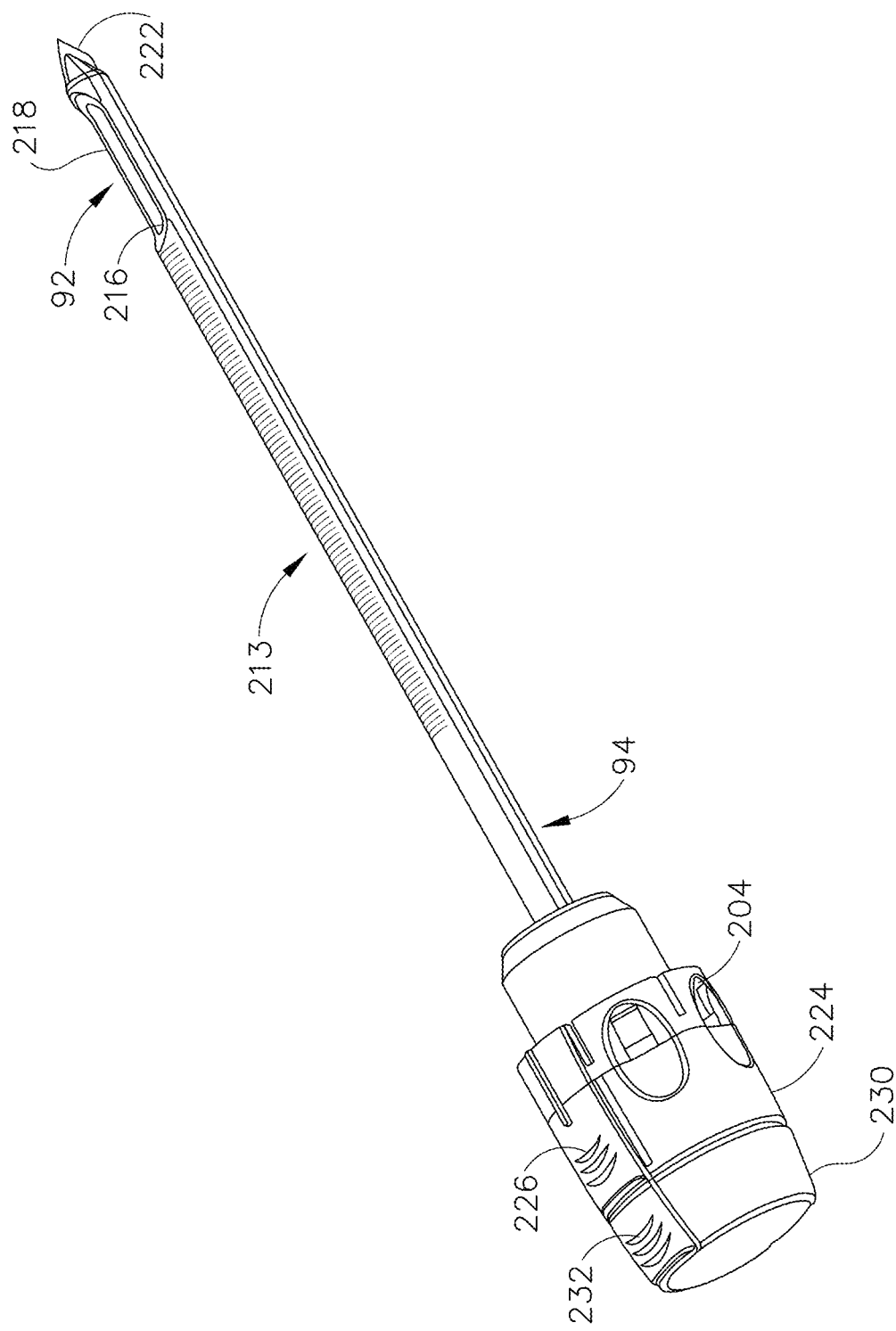
FIG. 7 depicts a perspective view of a obturator and cannula of the biopsy system of FIG. 1.
Figure 8:
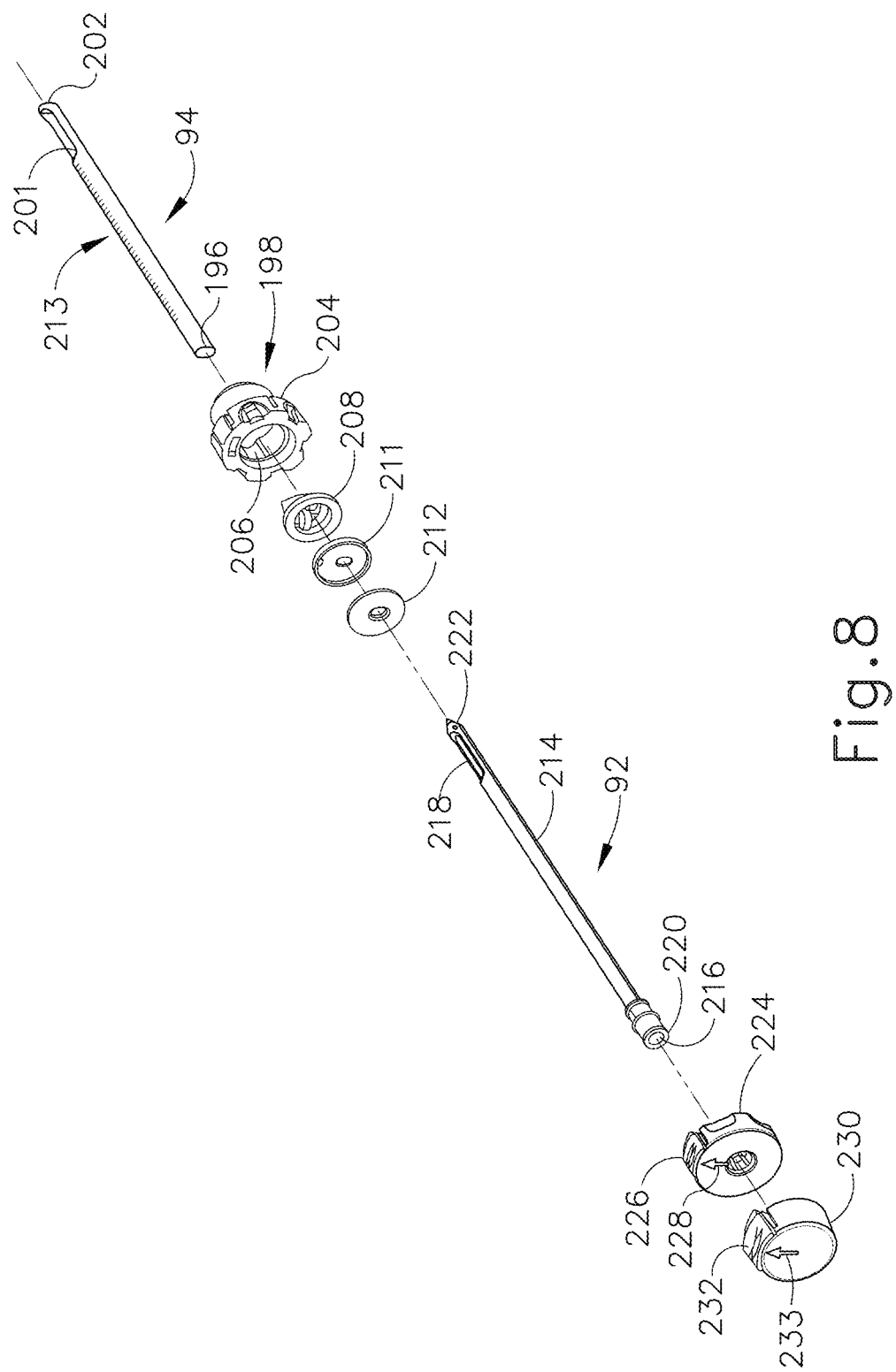
FIG. 8 depicts a perspective exploded view of the obturator and cannula of FIG. 7.
Figure 9:
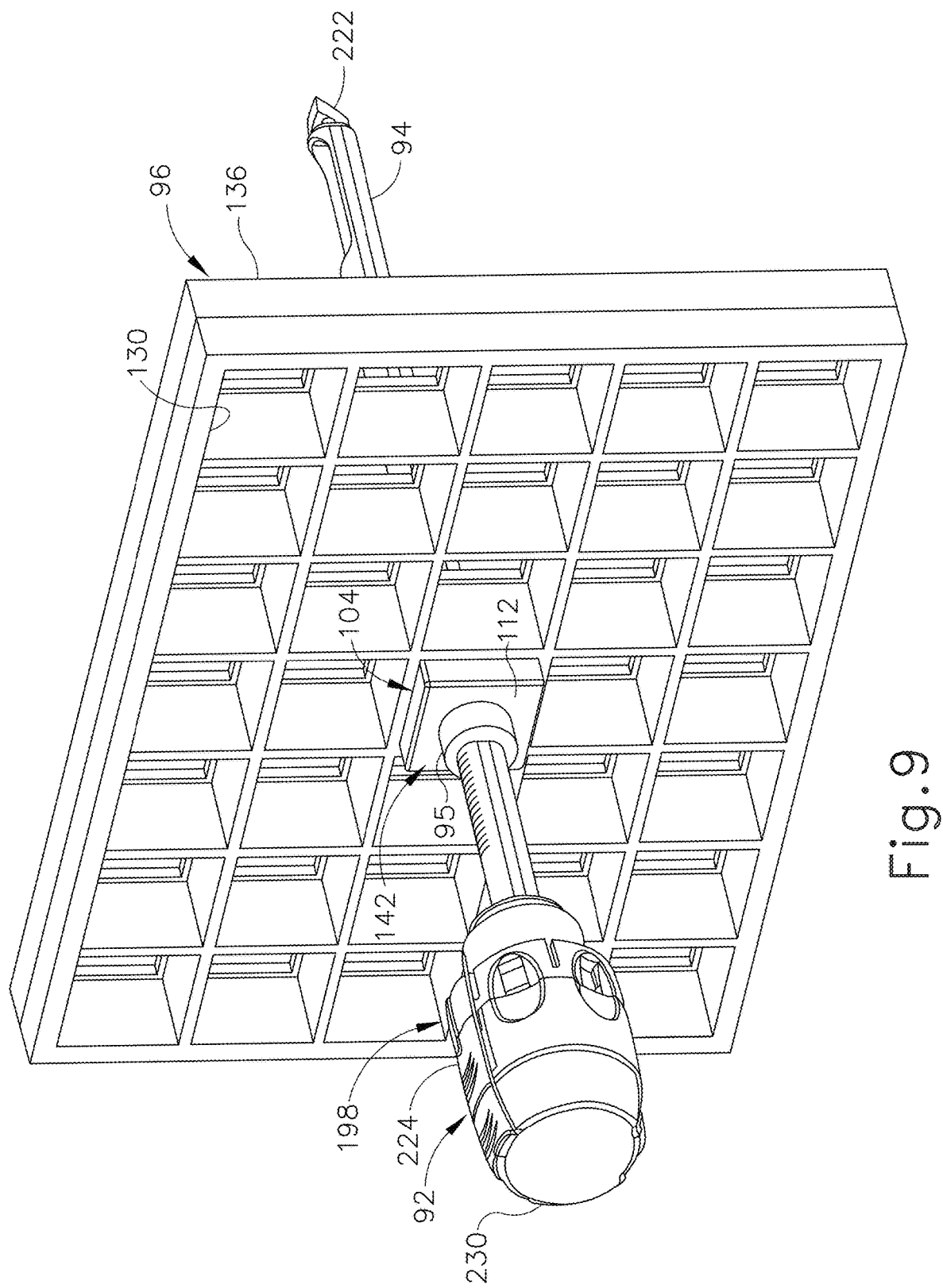
FIG. 9 depicts a perspective view of the obturator and cannula of FIG. 7 with a depth stop device of FIG. 1 inserted through the guide cube and grid plate of FIG. 6.

In the present example, a targeting set (89) comprising cannula (94) and obturator (92) is associated with probe (91). In particular, and as shown in FIGS. 7, 8, and 9, obturator (92) is slid into cannula (94) and the combination is guided through guide cube (104) to the biopsy site within the breast tissue. As shown in FIG. 3, obturator (92) is then withdrawn from cannula (94), then needle (90) of probe (91) is inserted in cannula (94), and then biopsy device (14) is operated to acquire one or more tissue samples from the breast via needle (90).

As best seen in FIG. 8, cannula (94) of the present example is proximally attached to cylindrical hub (198) and cannula (94) includes lumen (196) and lateral aperture (201) proximate to open distal end (202). Cylindrical hub (198) has exteriorly presented thumbwheel (204) for rotating lateral aperture (201). Cylindrical hub (198) has interior recess (206) that encompasses duckbill seal (208), wiper seal (211) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. For instance, obturator (92) includes a shaft (214) that includes fluid lumen (216) that communicates between imageable side notch (218) and proximal port (220). Shaft (214) is longitudinally sized such that piercing tip (222) extends out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (201) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 9, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop device (95). Depth stop device (95) may be of any suitable configuration that is operable to prevent cannula (94) and obturator (92) (or needle (90)) from being inserted further than desired. For instance, depth stop device (95) may be positioned on the exterior of cannula (94) (or needle (90)), and may be configured to restrict the extent to which cannula (94) is inserted into a guide cube. It should be understood that such restriction by depth stop device (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stop devices (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (201) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (201) of cannula (94) and the lateral aperture of needle (90). Severed tissue samples may be retrieved from biopsy device (14) in any suitable fashion.

It should be understood that although biopsy system (10) is discussed above as utilizing disposable probe assembly (91), other suitable probe assemblies and biopsy device assemblies may be utilized. By way of example only, other suitable biopsy devices may be configured and operable in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein. As yet another merely illustrative example, other suitable biopsy devices may be configured and operable in accordance with at least some of the teachings of U.S. Pub. No. 2010/0160824, the disclosure of which is incorporated by reference herein; U.S. Patent Pub. No. 2013/0144188, entitled "Biopsy Device with Slide-In Probe," published Jun. 6, 2013, the disclosure of which is incorporated by reference herein; U.S. Patent Pub. No. 2013/0324882, entitled "Control for Biopsy Device," published Dec. 5, 2013, the disclosure of which is incorporated by reference herein; U.S. Patent Pub. No. 2014/0039343, entitled "Biopsy System," published Feb. 6, 2014, the disclosure of which is incorporated by reference herein; and/or U.S. Patent Pub. No. 2015/0065913, entitled "Tissue Collection Assembly for Biopsy Device," published Mar. 5, 2015, the disclosure of which is incorporated by reference herein.

Still other suitable forms of biopsy devices that may be used in conjunction with the various alternative components of system (10) as described herein will be apparent to those of ordinary skill in the art.

IV. Exemplary Guide Cube

In some versions, a guide cube may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 4:
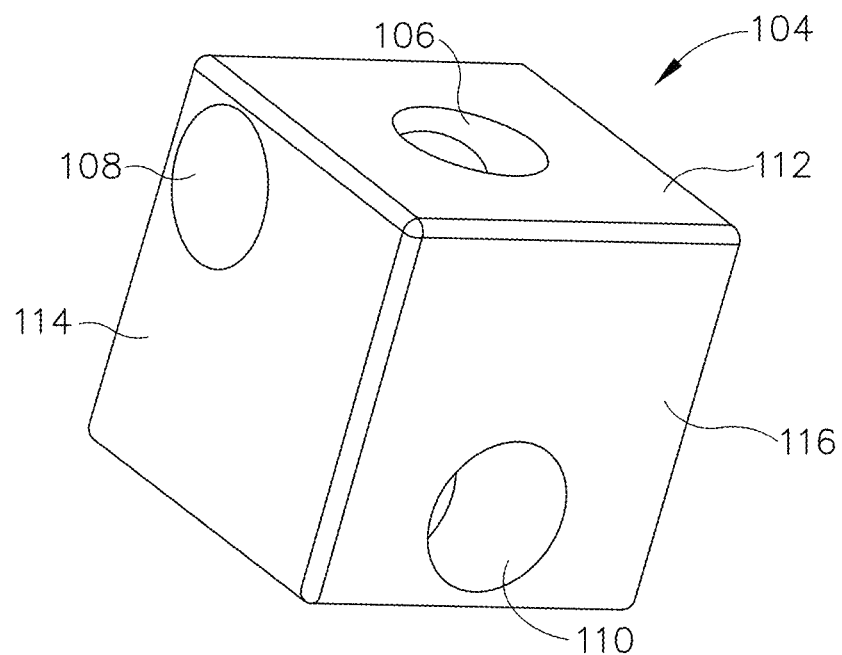
FIG. 4 depicts a perspective view of a two-axis rotatable guide cube of the biopsy system of FIG. 1.
Figure 5:
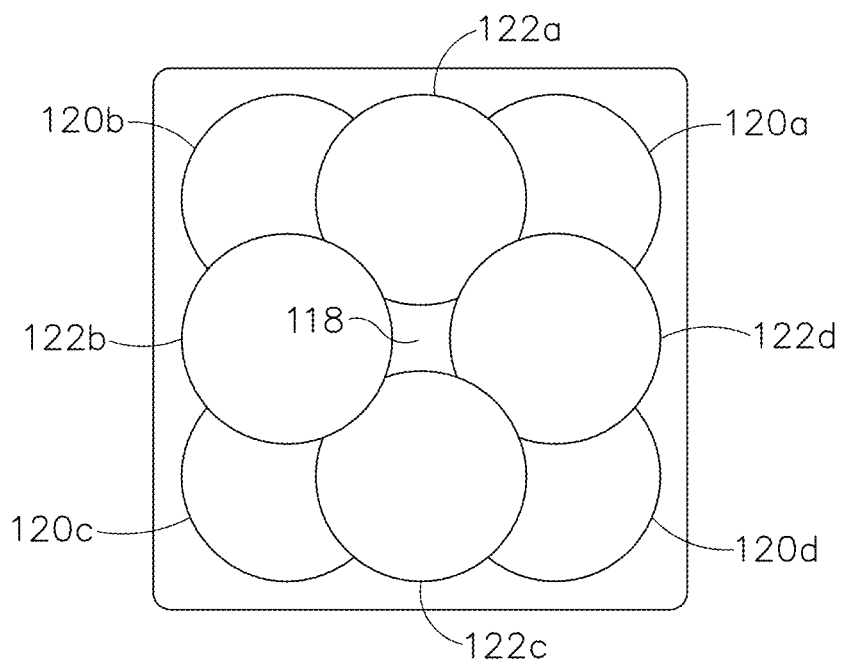
FIG. 5 depicts a diagram of nine guide positions achievable by the two-axis rotatable guide cube of FIG. 4.

In FIG. 4, guide cube (104) includes a central guide hole (106), a corner guide hole (108), and an off-center guide hole (110) that pass orthogonally to one another between respective opposite pairs of faces (112, 114, 116). By selectively rotating guide cube (104) in two axis, one of pairs of faces (112, 114, 116) may be proximally aligned to an unturned position and then selected proximal face (112, 114, 116) optionally rotated a quarter turn, half turn, or three quarter turn. Thereby, one of nine guide positions (118) (i.e., using central guide hole (106)), (120a-120d) (i.e., corner guide hole (108)), (122a-122d) (i.e., using off-center guide hole (110)) may be proximally exposed as depicted in FIG. 5.

Figure 6:
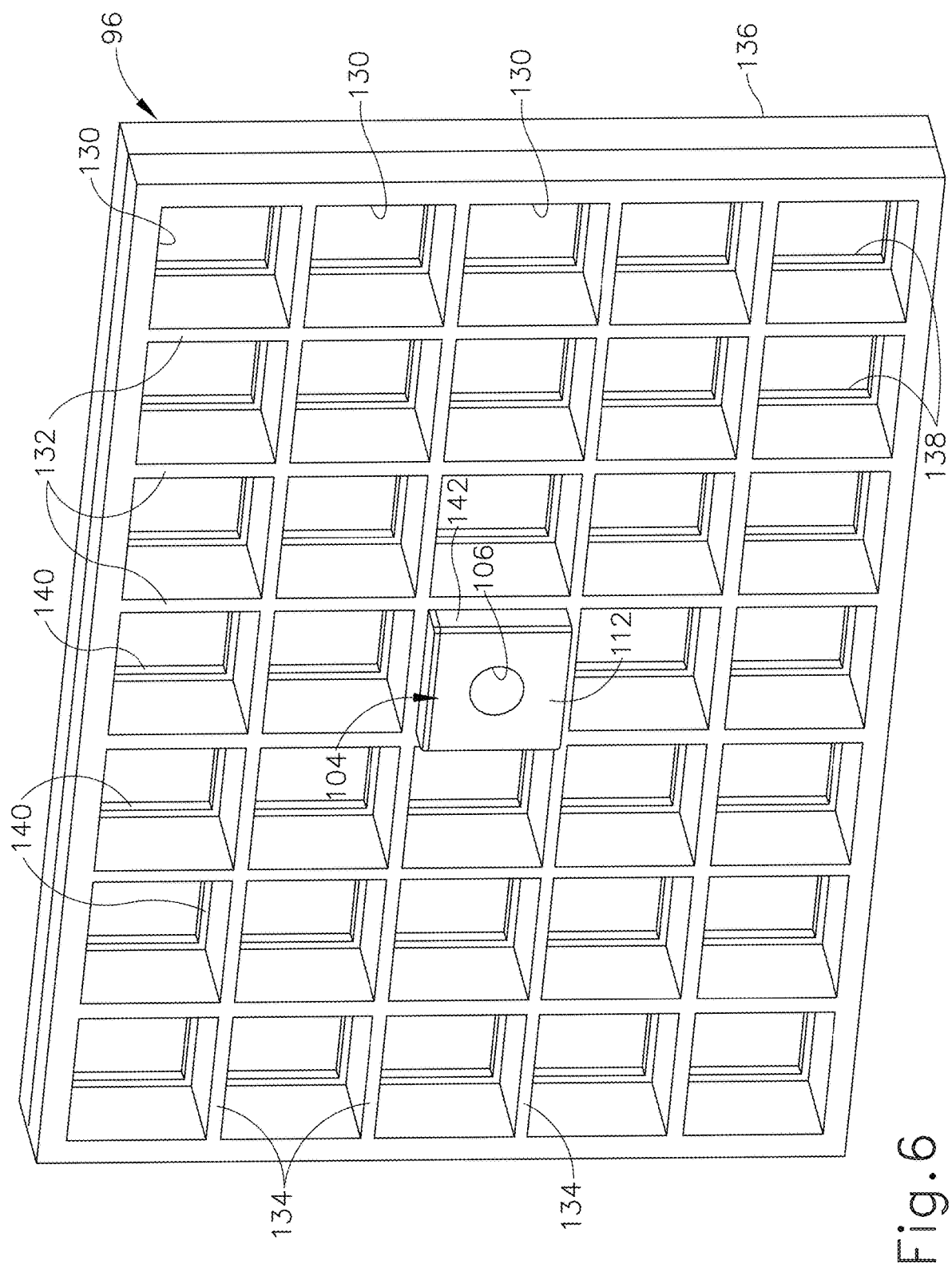
FIG. 6 depicts a perspective view of a two-axis rotatable guide cube into a lateral grid with the backing of the localization fixture of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

In some other versions, guide cube (104) is replaced with an alternative guide cube or other guide structure that is configured and operable in accordance with at least some of the teachings of U.S. Pat. Pub. No. 2015/0025414, entitled "Biopsy Device Targeting Features," published Jan. 22, 2015, the disclosure of which is incorporated by reference herein.

V. Exemplary Depth Stop Device With Dual Rotational Capability

In some instances, it may be desirable to provide a simplistic mechanical means of engaging the depth stop device with a cannula to control the depth of penetration within the breast of a patient. In some depth stop devices, such as depth stop device (95) described above, to engage cannula (94) an operator is restricted to rotating the device in a predetermined direction to lock, and subsequently unlock, depth stop device (95) relative to cannula (94). However, in some biopsy procedures, various equipment surrounding depth stop device (95) and/or cannula (94) may present challenges with rotating depth stop device (95) in a single direction. Accordingly, it may be desirable to provide a depth stop device that is capable of engaging cannula (94), and transitioning between a locked and unlocked state, by rotating the device in either direction. This may be beneficial to simplify and quicken the effective use of the depth stop device during a biopsy procedure. Furthermore, it may be desirable for the depth stop device to provide an operator with tactile feedback to indicate when the device is sufficiently rotated to a securely locked state. This may be beneficial to provide an operator with an interactive confirmation that the depth stop device is securely fastened to cannula (94) to thereby minimize the instance where the depth stop device and cannula (94) remain loosely engaged.

In other instances, it may be desirable for a depth stop device to provide a visual indicator to an operator of the proper orientation to install the device relative to the cannula. In some depth stop devices, such as depth stop device (95) described above, it may not be readily apparent to an operator which orientation is the correct alignment for proper installation of depth stop device (95) relative to cannula (94). Accordingly, it may be desirable for a depth stop device to clearly designate the proper positioning of the device in relation to cannula (94) and/or guide cube (104). This may be beneficial to further simplify and quicken the effective use of the depth stop device during a biopsy procedure.

It should be understood that the depth stop device described below may be readily incorporated into in any of the various targeting sets (89) and guide cubes (104) described above and in any of the various surgical procedures described in the various references described herein. In particular, the depth stop device examples described below may be used to assist in biopsy device needle targeting within a patient's breast using MRI guidance by permitting an operator to set a predetermined penetration depth. Other suitable ways in which the below-described depth stop devices may be used will be apparent to those of ordinary skill in the art in view of the teachings herein. By way of example only, in some examples depth stop device (1095) is configured and operable in accordance with at least some of the teachings of U.S. Pat. No. 8,568,333, entitled "Grid and Rotatable Cube Guide Localization Fixture for Biopsy Device," issued on Oct. 29, 2013, and U.S. application Ser. No. 15/499,950, entitled "Depth Stop Device for Use with Biopsy Targeting Assembly," filed on Apr. 28, 2017, the disclosures of which are incorporated by reference herein.

Figure 10:
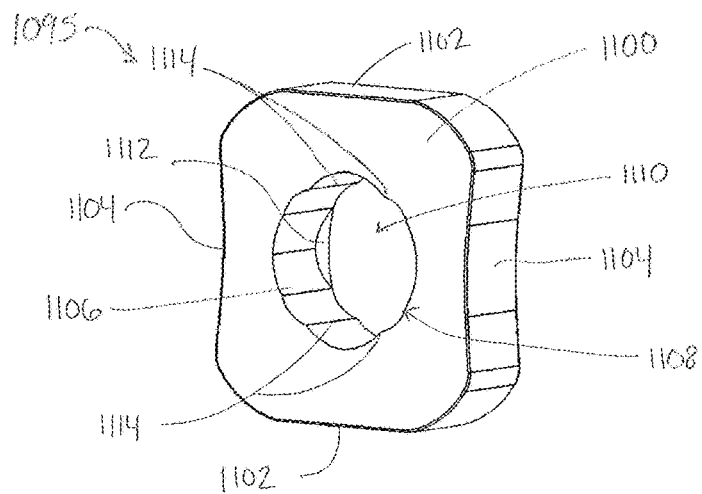
FIG. 10 depicts a perspective view of an alternative exemplary depth stop device.

FIG. 10 shows an exemplary alternative depth stop device (1095) for use in association with cannula (94) and/or guide cube (104) as similarly described above with respect to targeting set (89). It should be understood that, in many respects, depth stop device (1095) functions substantially similar to depth stop device (95) described above, except as otherwise described below. Depth stop device (1095) comprises an exterior housing (1100) comprising a relatively hard material such as ceramic. Housing (1100) includes a pair of ends (1102) and a pair of grip sides (1104). Grip sides (1104) are configured to be selectively manipulated by an operator to interchangeably transition depth stop device (1095) from an unlocked state to a locked state. Depth stop device (1095) further includes a receiving channel (1106) positioned within exterior housing (1100) and extending between a front-end opening (1108) and a rear-end opening (1110). Receiving channel (1106) is sized and configured to receive cannula (94) at front-end opening (1108) and through rear-end opening (1110). In particular, receiving channel (1106) generally defines an oval shape that corresponds with the oval-shaped profile of cannula (94) such that receiving channel (1106) is operable to receive cannula (94) without interference when lateral aperture (201) is aligned with either pair of ends (1102). Although not shown, it should be understood that receiving channel (1106) may be sized and shaped to have a different cross section than that illustrated, to support and facilitate the axial rotation of a cannula or biopsy instrument that doesn't have an oval/cylindrical profile.

Receiving channel (1106) further includes a pair of blades (1112) and a plurality of ramps (1114). Ramps (1114) are integral with depth stop device (1095) and extend axially along receiving channel (1106) and between openings (1108, 1110). Although ramps (1114) are shown as being integral with depth stop device (1095), it should be understood that ramps (1114) may be separate components attached to receiving channel (1106) as it will be apparent to those of ordinary skill in the art. Ramps (1114) are correspondingly positioned about receiving channel (1106) to permit depth stop device (1095) to receive cannula (94) therebetween without ramps (1114) interfering with cannula (94) entering into receiving channel (1106). In other words, ramps (1114) are configured to aid in orienting cannula (94) through receiving channel (1106) when received through front-end-opening (1108). Ramps (1114) have a lateral length or extension that extend into receiving channel (1106). Although this lateral length is shown in the present example as being relatively constant through the axial length of each ramp (1114), it should be understood that in other examples this lateral length can be varied as each ramp (1114) extends axially. For instance, in some examples each ramp (1114) may be configured as a series of protrusions oriented along a common axis. As will be described in greater detail below, with cannula (94) slidably received within receiving channel (1106), ramps (1114) are configured to briefly abut cannula (94) as depth stop device (1095) is selectively rotated in the clockwise or counterclockwise direction. With the rotation of depth stop device (1095), ramps (1114) are configured to generate a tactile feedback to an operator through the interaction between cannula (94) and ramps (1114). In other versions, ramps (1114) ramps (1114) are formed of elastomeric, resilient or deformable material. In this instance, as will be described in greater detail below, ramps (1114) are configured to deform outwardly upon encountering the outer surface of cannula (94) as depth stop device (1095) is selectively rotated.

Figure 11:
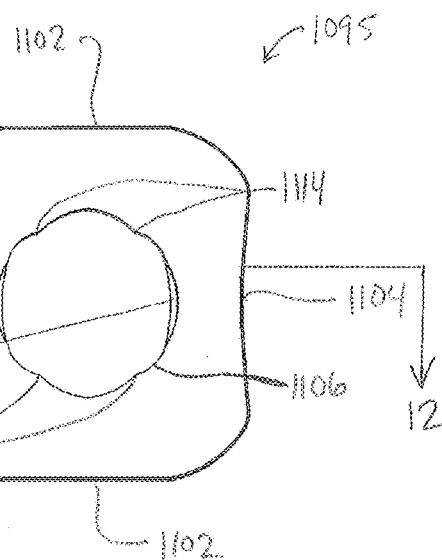
FIG. 11 depicts a front elevational view of the depth stop device of FIG. 10.

In the present example, as best seen in FIG. 11, four ramps (1114) are symmetrically positioned about receiving channel (1106), each having a substantially similar lateral extension into receiving channel (1106). The lateral extensions of each ramp (1114) into receiving channel (1106) is configured to be minimal so to allow depth stop device (1095) to rotate about cannula (94) without substantial hindrance. The substantially similar lateral extensions of ramps (1114) into receiving channel (1114) provide depth stop device (1095) with dual rotational capabilities. In other words, since ramps (1114) have similar lateral lengths, depth stop device (1095) is capable of rotating about cannula (94) in either direction as no particular ramp (1114) completely prevents depth stop device (1095) from rotating with cannula (94) positioned therein. In this instance, with cannula (94) being positioned within receiving channel (1106) and between ramps (1114), depth stop device (1095) is configured to selectively rotate relative to cannula (94), in either a clockwise or counterclockwise direction, and thereby transition from the unlocked state to the locked state. Although four ramps (1114) are shown, it should be understood that more or less ramps (1114) may be included along receiving channel (1106) as will be apparent to those of ordinary skill in the art in view of the teachings herein.

Figure 12:
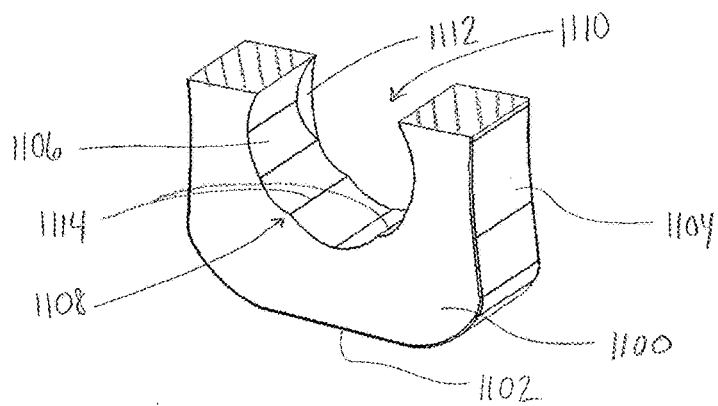
FIG. 12 depicts a perspective cross-sectional view of the depth stop device of FIG. 10, the cross section taken along line 12-12 of FIG. 11.

As seen in FIGS. 11-12, blades (1112) are similarly integral with depth stop device (1095) and extend longitudinally along receiving channel (1106). In particular, blades (1112) may be formed by a same material as depth stop device (1095) and extend between the pair of ends (1102), at rear-end opening (1110). Although blades (1112) are shown as being integral with depth stop device (1095), it will be apparent to those of ordinary skill in the art that blades (1112) may be separate components attached to receiving channel (1106). As best seen in FIG. 12, blades (1112) are shaped and sized to have a triangular cross-section that extends into receiving channel (1106) at a predetermined length to engage cannula (94), as will be described in greater detail below. Although not shown, blades (1112) may include various other suitable sizes and shapes along receiving channel (1106) as will be apparent to those of ordinary skill in the art in view of the teachings herein. As will be described in greater detail below, with cannula (94) slidably received within receiving channel (1106), blades (1112) are configured to engage cannula (94) when depth stop device (1095) is selectively rotated and transitioned from the unlocked state to the locked state. In this instance, with depth stop device (1095) in the locked state, blades (1112) are configured to securely grip cannula (94) to thereby inhibit cannula (94) from axially translating within receiving channel (1106), relative to depth stop device (1095), through the frictional engagement between blades (1112) and the outer surface of cannula (94).

Although use of the term "blades" herein may imply the presence of a sharp or pointed feature, it should be understood that in some examples blades (1112) are not necessarily sharp. For instance, in some examples blades (1112) include a rounded or otherwise blunt configuration to provide a compression or friction based stopping feature. In such examples, blades (1112) are configured to deform inwardly upon engaging the outer surface of cannula (94) to thereby securely bind depth stop device (1095) to cannula (94). Where blades (1112) are configured to deform, as a merely illustrative example, blades (1112) are formed of an elastomer material. Alternatively, in other versions, blades (1112) may be configured to deform the outer surface of cannula (94) upon depth stop device (1095) rotating to the locked state. In this instance, blades (1112) are formed of a generally rigid material that is resistant to deformation, such that the outer surface of cannula (94) deforms inwardly upon being engaged by blades (1112). In other words, blades (1112) are configured to dig in, or alternatively slice into, the outer surface of cannula (94) when depth stop device (1095) is transitioned from the unlocked state to the locked state. Although two blades (1112) are shown, it should be understood that more or less blades (1112) may be included along receiving channel (1106). For instance, in some examples depth stop device (1095) may include only a single blade (1112). In other examples, depth stop device (1095) may include a plurality of blades (1112), such as three or four. In still other examples, depth stop device (1095) may include any suitable number of blades (1112) as will be apparent to those of ordinary skill in the art in view of the teachings herein.

Figure 13A:
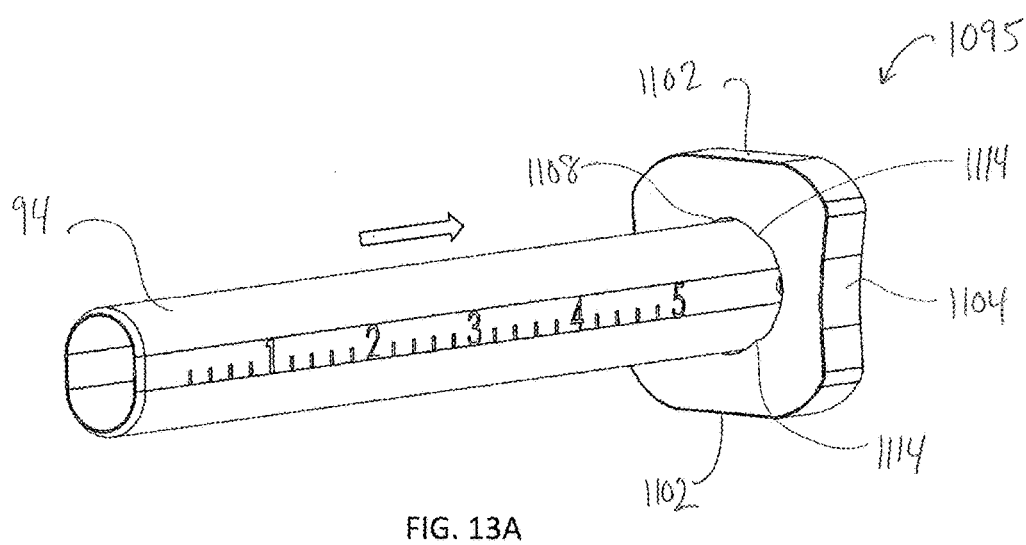
FIG. 13A depicts a perspective view of the depth stop device of FIG. 10, with a cannula of a device being inserted therein.

FIGS. 13A-14B show an exemplary us of depth stop device (1095) in connection with cannula (94). In the present example, as seen in FIG. 13A, an operator slidably inserts cannula (94) into receiving channel (1106) of depth stop device (1095) until depth stop device (1095) is aligned with a desired depth as indicated by longitudinally spaced measurement indicia (213) along the outer surface of cannula (94). As mentioned above, longitudinally spaced measurement indicia (213) of cannula (94) visually, and perhaps physically (e.g., via equally spaced indentations in the outer surface of cannula (94)), provide a means to locate depth stop device (1095) relative to cannula (94). Although not shown, cannula (94) is inserted into depth stop device (1095) with lateral aperture (201) aligned within receiving channel (1106) facing either pair of ends (1102). In this instance, as best seen in FIG. 14A, the outer surface of cannula (94) fits between and alongside ramps (1114) such that depth stop device (1095) is in the unlocked state.

Figure 13B:
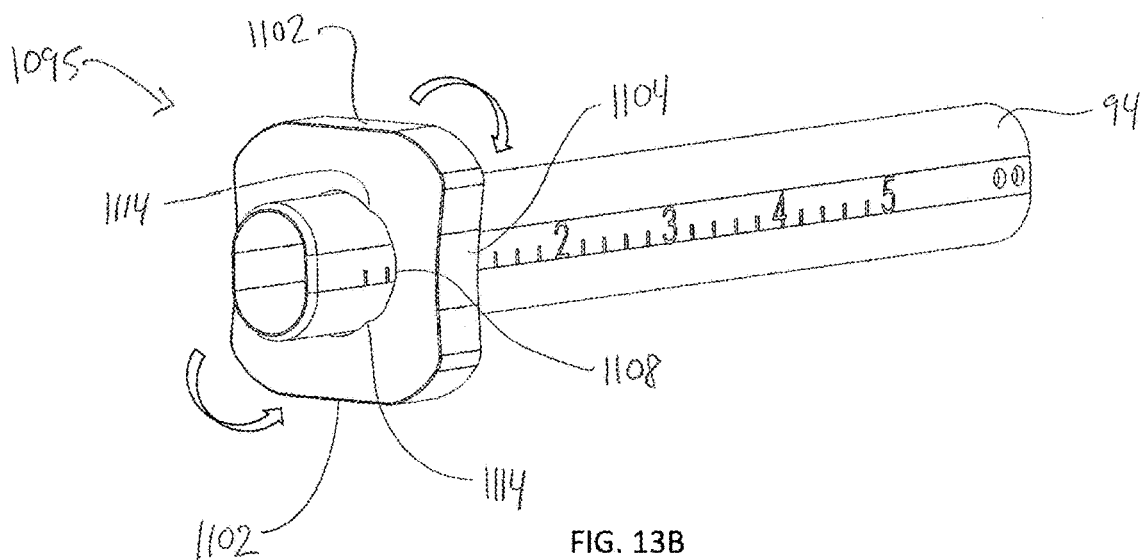
FIG. 13B depicts a perspective view of the depth stop device of FIG. 10, with the cannula inserted into the depth stop device at a desired depth and the depth stop device in an unlocked state, the depth stop device being capable of rotating clockwise or counterclockwise to securely grasp the cannula therein.

With depth stop device (1095) positioned along cannula (94) at the desired depth, an operator grasps pair of grip sides (1104) and selectively rotates depth stop device (1095) either in the clockwise or counterclockwise direction, as seen in FIG. 13B. With the lateral extensions of ramps (1114) being substantially similar, an operator may selectively determine which rotational direction is preferred to transition depth stop device (1095) from the unlocked state to the locked state. As depth stop device (1095) is rotated 90 degrees in either direction, ramps (1114) briefly abut against the outer surface of cannula (94) thereby generating a tactile feedback that is perceived by an operator through the grasp of grip sides (1104). In this instance, the outer surface of cannula (94) is deformed inwardly, momentarily, when encountering ramps (1114) as depth stop device (1095) is rotated. Once ramps (1114) surpass abutting against the outer surface of cannula (94), the outer surface of cannula (94) reassumes an oval shape. In other versions, with ramps (1114) being formed of elastomeric or deformable material, ramps (1114) deform outwardly relative to receiving channel (1106) when encountering the outer surface of cannula (94). In such examples, once ramps (1114) rotatably surpass contacting the outer surface of cannula (94), ramps (1114) are released from physical constraint and reassume a laterally extending profile into receiving channel (1106). As it will be apparent to those of ordinary skill in the art, the orientations and geometries depicted are merely illustrative. Furthermore, the degree of rotation to transition depth stop device (1095) from the unlocked state to the locked state may be more or less than 90 degrees.

Figure 13C:
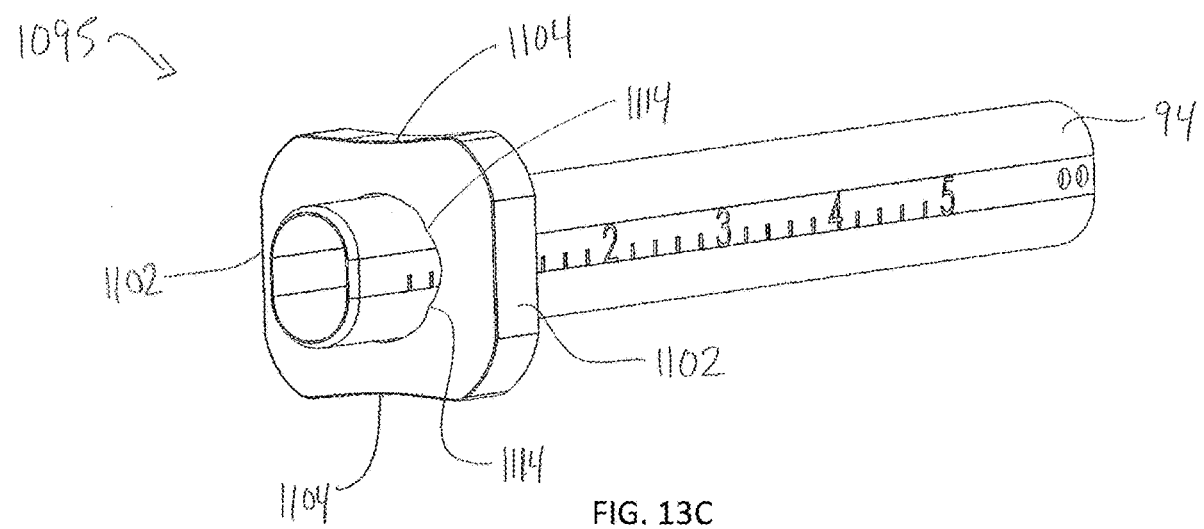
FIG. 13C depicts a perspective view of the depth stop device of FIG. 10, with the depth stop device rotated to a locked state and thereby securely engaged with the cannula positioned therein.
Figure 14A:
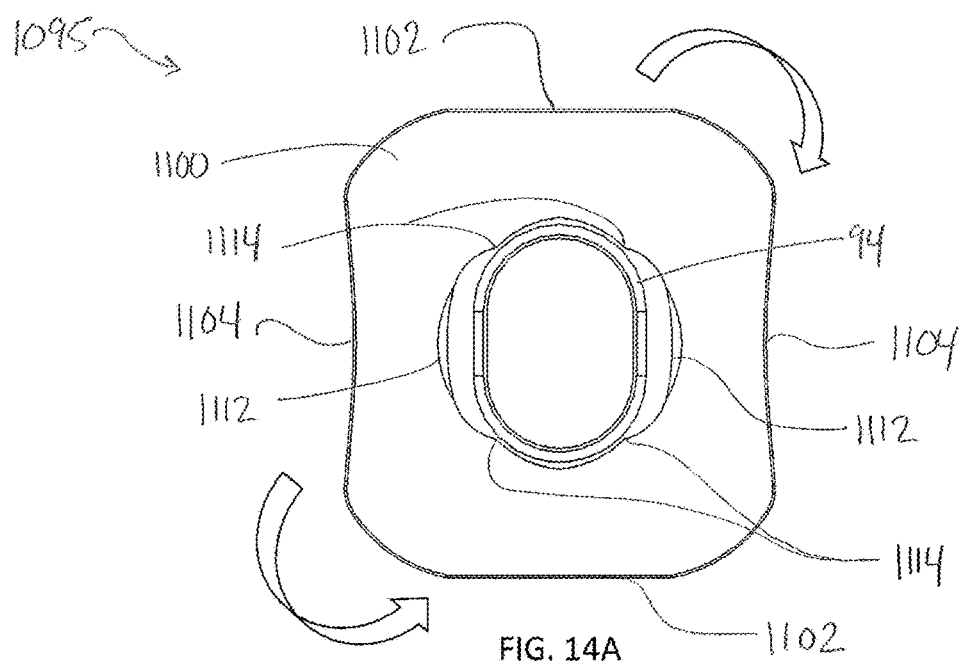
FIG. 14A depicts a front elevational view of the depth stop device of FIG. 10, with a cannula of a device inserted therein.
Figure 14B:
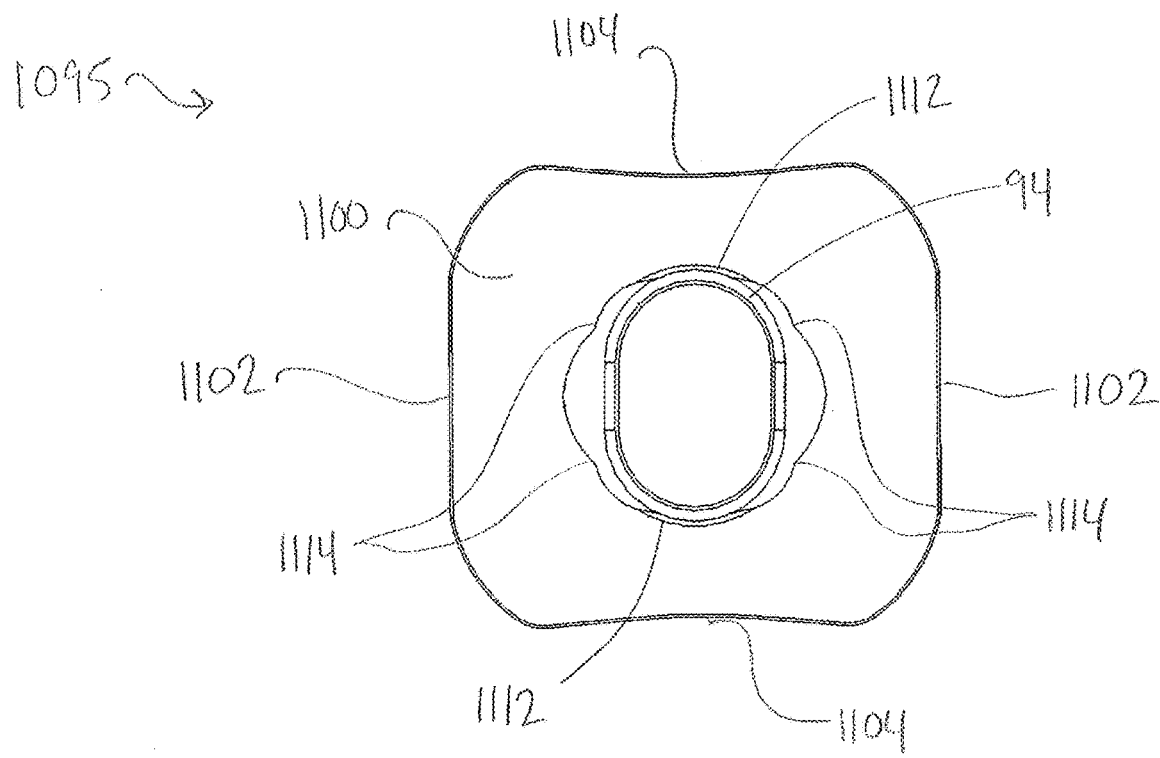
FIG. 14B depicts a front elevational view of the depth stop device of FIG. 10, with the depth stop device rotated to securely grasp the cannula of the device positioned therein.

Once an operator experiences the tactile feedback produced from the interaction between ramps (1114) and cannula (94), an operator becomes informed that depth stop device (1095) is now in the locked state, as seen in FIG. 13C. With depth stop device (1095) in the locked state, blades (1112) are actively engaged with cannula (94) by slicing into, or digging into, the outer surface of cannula (94) to thereby securely bind cannula (94) to depth stop device (1095), as seen in FIG. 14B. In this instance, with blades (1112) extending through the outer surface of cannula (94), cannula (94) is prevented from axially translating within receiving channel (1106) while depth stop device (1095) is in the locked state.

During a biopsy procedure, or after conclusion of the procedure, an operator may desire to release depth stop device (1095) from cannula (94) to thereby adjust depth stop device (1095) relative to cannula (94). In this instance, an operator selectively rotates depth stop device (1095) in either direction, clockwise or counterclockwise, to subsequently transition depth stop device (1095) to the unlocked state. Accordingly, it should be understood that it is immaterial which rotational direction depth stop device (1095) was initially rotated towards when transitioning depth stop device (1095) to the locked state. By rotating depth stop device (1095) 90 degrees in either rotational direction, blades (1112) are removed from the engagement with cannula (94) such that blades (1112) are no longer slicing, or digging, into the outer surface of cannula (94).

Furthermore, as grip sides (1104) are grasped and selectively maneuvered to rotate depth stop device (1095) to the unlocked state, an operator perceives tactile feedback from the abutting interaction between ramps (1114) and the outer surface of cannula (94). In this instance, ramps (1114) briefly abut against the outer surface of cannula (94) thereby generating a tactile feedback that is perceived by an operator through the grasp of grip sides (1104). Similar to when depth stop device (1095) was rotated towards the locked state, the outer surface of cannula (94) is deformed inwardly when encountering ramps (1114) as depth stop device (1095) is rotated towards the unlocked state. Once ramps (1114) surpass abutting against the outer surface of cannula (94), the outer surface of cannula (94) reassumes an oval shape. Alternatively, as described above, in some examples the outer surface of cannula (94) remains relatively non-deformed while ramps (1114) deform. Regardless of the particular configuration of ramps (1114), the tactile feedback generated as depth stop device (1095) is transitioned to the unlocked state is identical to the initial tactile feedback experienced by the operator when depth stop device (1095) was rotated towards the locked state. It should be understood that the tactile feedback is generated irrespective of the rotational direction that depth stop device (1095) is rotated towards, due to the numerous ramps (1114) rotatably positioned about receiving channel (1106) such that the outer surface of cannula (94) will inevitably encounter one or more of the numerous ramps (1114).

Figure 15:
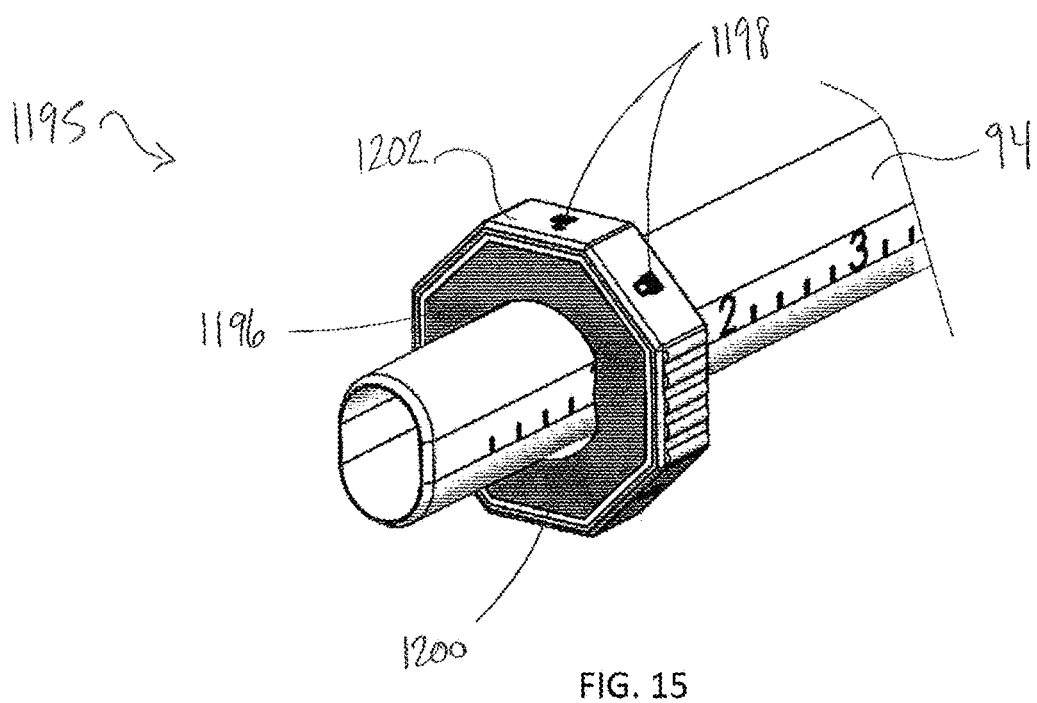
FIG. 15 depicts another alternative exemplary depth stop device, including a locking identifier.

FIG. 15 shows an alternative exemplary depth stop device (1195). Except as otherwise described below, depth stop device (1195) may be configured and operable just like depth stop device (1095) described above. Depth stop device (1195) includes an orientation identifier (1196) and a locking identifier (1198) in the form of a symbol, etching, and/or color, etc. Orientation identifier (1196) is positioned along an exterior housing (1200) and is operable to provide an operator with a visual indication of the respective locations of a front-end opening (1208) and a rear-end opening (1210). In the present example, orientation identifier (1196) comprises a colored exterior housing (1200) along the side of depth stop device (1195) adjacent front-end opening (1208). In this instance, orientation identifier (1196) readily informs an operator of the proper face/side of depth stop device (1195) that cannula (94) should be inserted through. In use, an operator will easily distinguish front-end opening (1208) from rear-end opening (1210) due to the position of orientation identifier (1196) which further simplifies and quickens the effective use of depth stop device (1095) during a biopsy procedure. Although orientation identifier (1196) is shown in the form of a color, it will be apparent to those of ordinary skill in the art that orientation identifier (1196) can take various suitable forms that will visually or physically indicate the front side of depth stop device (1195) from the rear side.

As further seen in FIG. 15, depth stop device (1195) further includes a locking identifier (1198) in the form of a symbol. Depth stop device (1195), similar to depth stop device (95) and dissimilar from depth stop device (1095), is configured to rotate in a single direction to securely grip cannula (94) positioned therein and transition from the unlocked state to the locked state. In the present example, locking identifier (1198) is positioned along exterior housing (1200), particularly along pair of ends (1202). Locking identifier (1198) is operable to provide an operator with a visual indication of which rotational direction to move depth stop device (1195) to lock depth stop device (1195) relative to cannula (94). In use, with cannula (94) slidably inserted through depth stop device (1195), an operator will easily identify the proper direction to rotate depth stop device (1195) relative to cannula (94) to thereby lock, and subsequently unlock, depth stop device (1195) from the frictional engagement with cannula (94). Although locking identifier (1198) is shown in the form of symbols positioned along pair of ends (1202), it will be apparent to those of ordinary skill in the art that locking identifier (1198) can take various suitable forms and be positioned along various locations along depth stop device (1195) to visually or physically indicate the proper rotational direction to lock and unlock depth stop device (1195).

Figure 16:
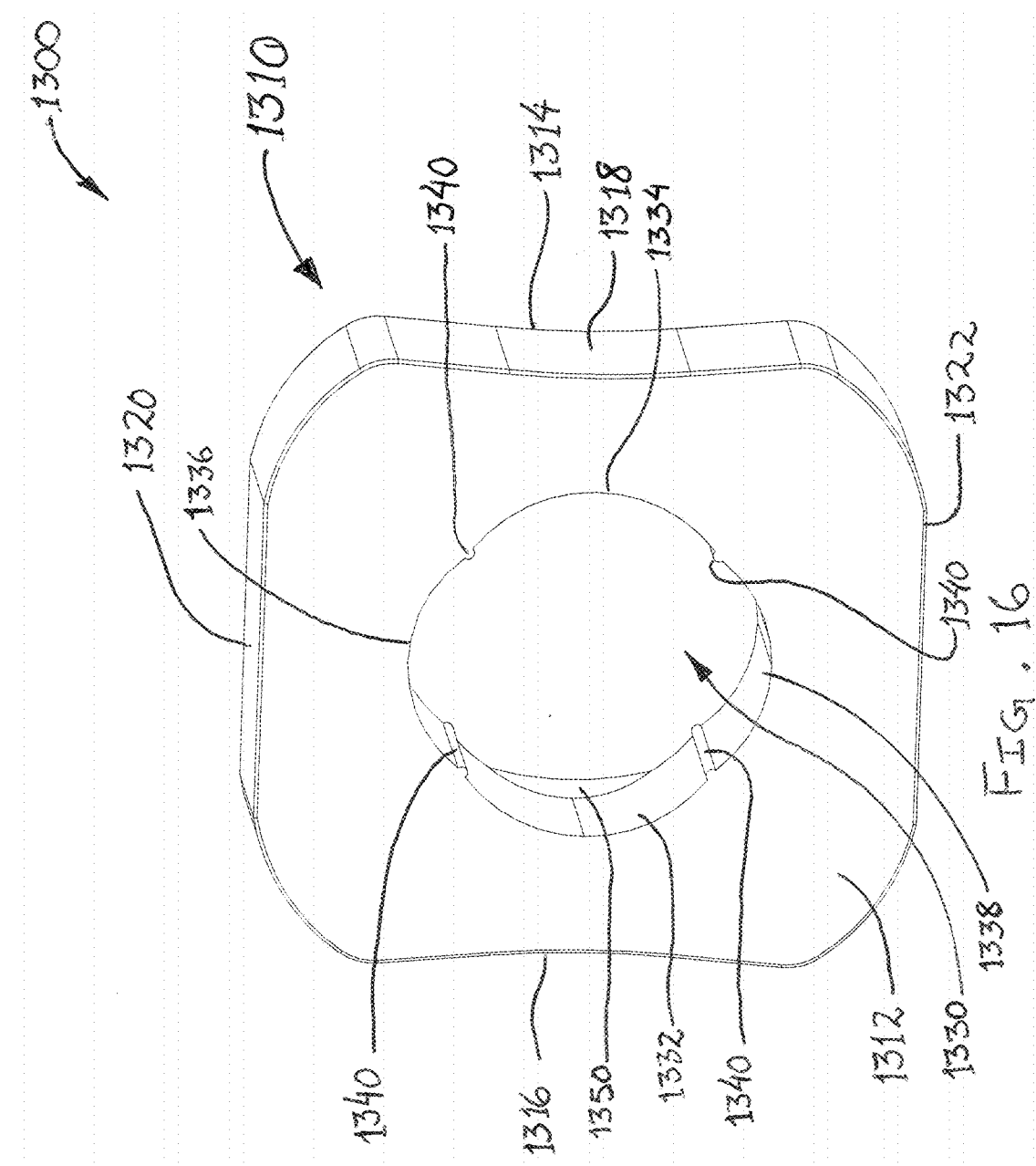
FIG. 16 depicts a perspective view of yet another alternative exemplary depth stop device.
Figure 17:
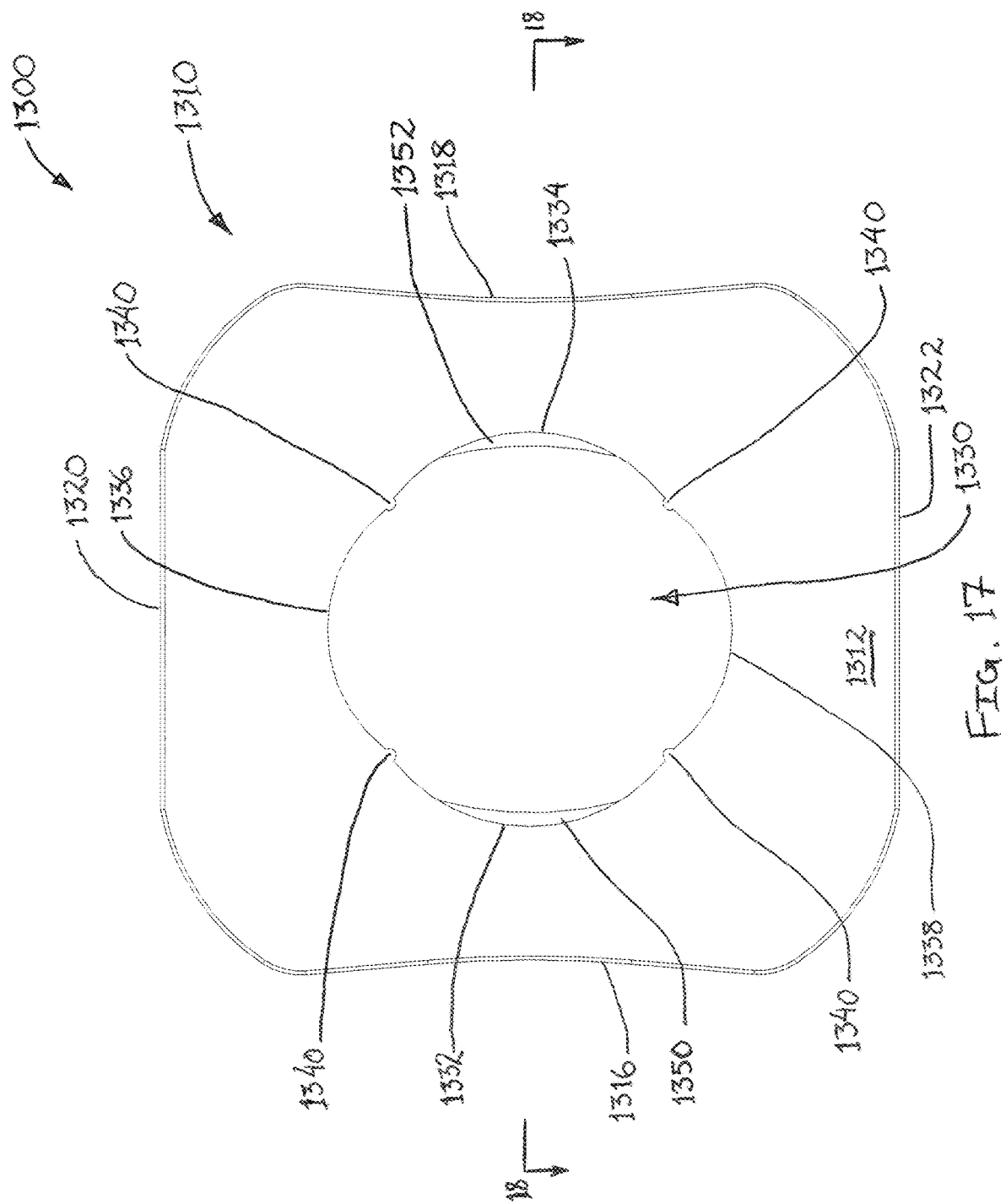
FIG. 17 depicts a front elevational view of the depth stop device of FIG. 16.
Figure 18:
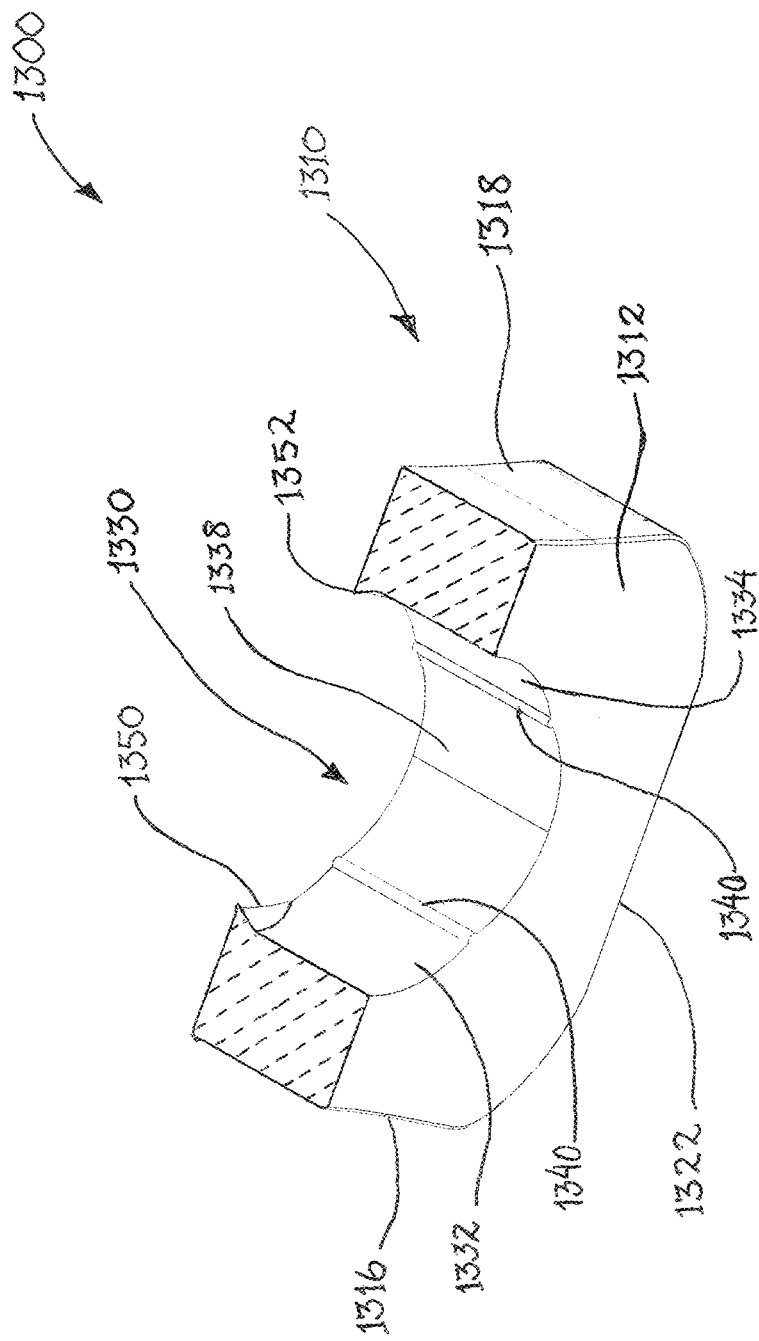
FIG. 18 depicts a perspective cross-sectional view of the depth stop device of FIG. 16, the cross-section taken along line 18-18 of FIG. 17.

FIGS. 16-18 show an alternative depth stop device (1300) that may be used with cannula (94) described above. Depth stop device (1300) is generally substantially similar to depth stop device (1095) described above unless otherwise specifically noted herein. Depth stop device (1300) includes a generally rectangular body (1310) that defines a receiving channel (1330) extending therethrough. Body (1310) includes a distal face (1312), a proximal face (1314) opposite of distal face (1312), a left side (1316), a right side (1318), a top side (1320) and a bottom side (1322). Sides (1316, 1318, 1320, 1322) extend between distal face (1312) and distal face (1314) to define a generally solid rectangular shape. In some examples, one or more sides (1316, 1318,

1320, 1322) can be shaped to enhance gripping of body (1310). For instance, in the present examples left side (1316) and right side (1318) both form a slight concave curvature to provide an area for gripping. Of course, other configurations to enhance gripping may be used as will be apparent to those of ordinary skill in the art in view of the teachings herein.

In the present example, body (1310) is comprised of a hard material such as a ceramic. However, it should be understood that in other examples (1310) can alternatively comprise other hard materials such as metals, hard plastics, and the like. In still other examples, body (1310) can be comprised of relatively soft materials. As will be described in greater detail below, in examples where body (1310) comprises a relatively soft material, this may be used to impact the properties of other portions of depth stop device (1300).

Receiving channel (1330) is disposed around the center point of body (1310). Receiving channel (1330) generally extends through body (1310) from distal face (1312) to proximal face (1314) and is sized to receive cannula (94). The shape of receiving channel (1330) generally corresponds to two oval shapes superimposed on each other at 90 degrees. In particular, receiving channel (1330) is generally defines by a left side concave surface (1332), a right side concave surface (1334), a top concave surface (1336) and a bottom concave surface (1338). Each concave surface (1332, 1334, 1336, 1338) is interconnected with another adjacent concave surface (1332, 1334, 1336, 1338) to form the overall shape of receiving channel (1330). Moreover, concave surfaces (1332, 1334, 1336, 1338) are arranged in pairs such that left concave surface (1332) is opposite of right concave surface (1334) and top concave surface (1336) is opposite of bottom concave surface (1338). As will be described in greater detail below, this configuration is generally configured to correspond to the shape of cannula (94) so that cannula (94) can be disposed between either a combination of left concave surface (1332) and right concave surface (1334) or top concave surface (1336) and bottom concave surface (1338).

At the intersection of each concave surface (1332, 1334, 1336, 1338), body (1310) defines a rib (1340), ramp feature or detent. Due to this configuration, each rib (1340) is oriented at a 90-degree angle relative to another adjacent rib (1340). Ribs (1340) are also oriented at a 45-degree angle relative to a center axis passing through either sides (1316, 1318) or sides (1320, 1322). As will be described in greater detail below, ribs (1340) are generally configured to provide tactile feedback to an operator when body (1310) is rotated relative to cannula (94) such that ribs (1340) snap over cannula (94) as body (1310) is rotated into various positions relative to cannula (94).

In the present example, ribs (1340) are integral with body (1310) such that ribs (1340) have similar material properties as body (1310). As described above, body (1310) in the present example comprises a hard material such as ceramic. Accordingly, it should be understood that ribs (1340) in the present example likewise have hard material properties. As also described above, in other examples the material of body (1310) can be varied to change the material properties thereof. Thus, in examples where body (1310) is a soft material, it should be understood that ribs (1340) can likewise have soft material properties. In other examples, ribs (1340) can be entirely separate from body (1310) and fastened thereto by various securing means such as adhesive bonding, mechanical fastening, and/or etc. In such examples, the material properties of ribs (1340) can be varied independently of body (1310). For instance, in some examples body (1310) can remain hard as it is in the present example. Meanwhile, ribs (1340) can be comprised of an elastomeric material to have elastomeric material properties. Of course, other combinations of materials and material properties can be used as will be apparent to those of ordinary skill in the art in view of the teachings here.

Depth stop device (1300) further includes a pair of blades (1350, 1352). In the present example, a left blade (1350) is positioned opposite of a right blade (1352). Each blade (1350, 1352) extends laterally from a corresponding concave surface (1332, 1334). In other words, left blade (1350) extends laterally from left concave surface (1332) into channel (1330), while right blade (1352) extends laterally from right concave surface (1334) into channel (1330).

In the present example, blades (1350, 1352) are integral with body (1310) such that blades (1350, 1352) comprise the same material as body (1310). As described above, body (1310) of the present example comprises a hard material such as ceramic. Accordingly, it should be understood that blades (1350, 1352) of the present example likewise comprise a hard material such as ceramic. This hard configuration of blades (1350, 1352) generally permits blades to dig into a portion of cannula (94), which can be relatively soft relative to blades (1350, 1352). As will be described in greater detail below, this digging in functionality can be used to selectively lock depth stop device (1300) at a specific axial position along the length of cannula (94).

Although blades (1350, 1352) of the present example are described herein as having hard material properties, it should be understood that in other examples, the particular properties of blades (1350, 1352) can be varied to provide different operational features. For instance, in some examples it may be desirable for blades (1350, 1352) to bind with cannula (94) instead of digging in. In such examples, blades (1350, 1352) can be comprised of a relatively soft material having resilient or elastomeric properties. It should be understood that this configuration may be accomplished in a variety of ways. For instance, in some examples the material of body (1310) can be changed to alter the material of blades (1350, 1352). In other examples, blades (1350, 1352) can be separately attached to body (1310) such that the material of blades (1350, 1352) can be varied independently of the material of body (1310). Of course, various other configurations will be apparent to those of ordinary skill in the art in view of the teachings herein.

Depth stop device (1300) is generally used in a biopsy procedure as described above with respect to depth stop device (1095). For instance, cannula (94) can be initially inserted into channel (1330) of depth stop device (1300) with body (1310) positioned in an unlocked position relative to cannula (94). In the unlocked position, top side (1320) and bottom side (1322) are generally oriented horizontally. It should be understood that "horizontally" used herein is only in reference to the generally used position of cannula (94) shown in FIG. 13A. In this position, cannula (94) is oriented so that the oval shape of cannula (94) has is oriented vertically so that the longitudinal axis of the oval is perpendicular to the horizon. Thus, in uses where the operating position of cannula (94) is varied, the orientation of depth stop device (1095) can likewise be varied.

Regardless of the particular orientation of cannula (94), when depth stop device (1300) is positioned in the unlocked position, top concave surface (1336) and bottom concave surface (1338) are both aligned to receive the top and bottom portion of cannula (94) such that the longitudinal axis of the oval shape of cannula (94) passes through top concave surface (1336) and bottom concave surface (1338). This permits depth stop device (1300) to be slid axially along the length of cannula (94) to a desired insertion depth corresponding to a Z-axis position. In this position, ribs (1340) generally restrict inadvertent rotation of body (1310) relative to cannula (94).

Once an operator has positioned depth stop device (1300) along the axial length of cannula (94) to a desired depth of insertion, an operator may desire to transition depth stop device (1300) to a locked position to lock depth stop device (1300) onto cannula (94) at the desired depth of insertion. To transition depth stop device (1300) to the locked position, body (1310) can be rotated in either a clockwise or counterclockwise direction. As body (1310) is rotated, some force may be applied to overcome the force supplied by ribs (1340). Once body (1310) is rotated approximately 90 degrees relative to cannula (94), depth stop device (1300) will be in the locked position.

When depth stop device (1300) is in the locked position, left side (1316) and right side (1318) are oriented horizontally instead of top side (1320) and bottom side (1322) being oriented horizontally. Thus, in this position, left concave surface (1332) and right concave surface (1334) receive the top and bottom portions of cannula (94). Because blades (1350, 1352) are associated with left concave surface (1332) and right concave surface (1334), blades (1350, 1352) also dig into the surface of cannula (94). This configuration secures depth stop device (1300) to the desired depth of insertion along the axial length of cannula (94). Cannula (94) and depth stop device (1300) may then be used in an MRI guided breast biopsy procedure as described above.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for use with a biopsy instrument, the apparatus comprising: (a) a housing defining a channel sized and shaped to receive a cannula of the biopsy instrument, wherein the housing is configured to be selectively rotatable such that the housing is operable to transition from an unlocked state to a locked state when rotated; (b) at least two ramps extending inwardly from the housing into the channel, wherein the at least two ramps are configured to abut the cannula when the housing is selectively rotated to thereby generate a tactile feedback; (c) at least two blades extending inwardly from the housing into the channel, wherein the two blades are configured to engage the cannula upon the selective rotation of the housing; wherein the housing is configured to restrict the depth of insertion of the cannula through the channel when the housing is in the locked state.

Example 2

The apparatus of Example 1, wherein the housing is configured to be selectively rotatable in a clockwise direction or counterclockwise direction such that the housing is operable to transition from the unlocked state to the locked state when rotated in either direction.

Example 3

The apparatus of Example 2, wherein the housing is operable to transition from the locked state to the unlocked state when selectively rotated in the clockwise direction or counterclockwise direction.

Example 4

The apparatus of any one or more of Examples 1 through 3, wherein the housing in the unlocked state is configured to permit translation of the cannula through the channel along a translation axis, wherein the translation axis is perpendicular to a longitudinal axis of the cannula.

Example 5

The apparatus of Example 4, wherein the housing in the locked state is configured to prevent translation of the cannula through the channel along the translation axis.

Example 6

The apparatus of any one or more of Examples 1 through 5, wherein the housing includes a front opening and a rear opening, wherein the front opening is configured to receive the cannula.

Example 7

The apparatus of Example 6, wherein the at least two blades extend into the channel proximate to the rear opening.

Example 8

The apparatus of Example 7, wherein the at least two ramps are axially positioned about the channel, wherein the at least two ramps extend along the channel between the front and rear openings.

Example 9

The apparatus of Example 8, wherein the housing includes a pair of grip sides configured to be selectively maneuvered to transition the housing from the unlocked state to the locked state.

Example 10

The apparatus of any one or more of Examples 1 through 9, wherein the channel defines a shape in correspondence with a profile of the cannula.

Example 11

The apparatus of Example 10, wherein the shape of the channel is oval-shaped to accommodate an oval-shaped cross-section of the cannula.

Example 12

The apparatus of any one or more of Examples 1 through 11, wherein the at least two ramps are unitary and integral with the housing.

Example 13

The apparatus of any one or more of Examples 1 through 12, wherein the at least two blades are unitary and integral with the housing.

Example 14

The apparatus of any one or more of Examples 1 through 13, wherein the at least two blades are formed of an elastomer material, wherein the at least two blades are configured to deform when the housing is selectively rotated to the locked state.

Example 15

The apparatus of any one or more of Examples 1 through 14, wherein the at least two blades are configured to deform the cannula when the housing is selectively rotated to the locked state.

Example 16

The apparatus of any one or more of Examples 1 through 15, wherein the housing further includes a first visual identifier.

Example 17

The apparatus of Example 16, wherein the first visual identifier is configured to indicate the direction of rotation to interchangeably transition the housing from the unlocked state to the locked state.

Example 18

The apparatus of Example 6 or 16, wherein the housing further includes a second visual identifier.

Example 19

The apparatus of Example 18, wherein the second visual identifier is configured to identify the front opening from the rear opening such that the front opening is configured to slidably receive the cannula.

Example 20

The apparatus of any one or more of Examples 1 through 19, wherein the housing is configured to abut a guide cube associated with an MRI patient fixture to thereby cease axial movement of the housing relative to a patient.

Example 21

An apparatus for guiding a targeting sleeve into a breast of a patient supported upon a patient support surface, the apparatus comprising: (a) housing, wherein the housing defines a sleeve opening sized and configured to slidably receive the targeting sleeve, wherein the housing is configured to securely attach to the targeting sleeve through rotation with the targeting sleeve received in the sleeve opening; (b) a ramp, wherein the ramp extends into the sleeve opening and is configured to engage the targeting sleeve when the housing is rotated, wherein the ramp is configured to deform the targeting sleeve inwardly when engaging the targeting sleeve, wherein the ramp is configured to produce a tactile feedback to an operator when engaging the targeting sleeve; (c) a blade, wherein the blade extends into the sleeve opening and is configured to engage the targeting sleeve when the housing is rotated to thereby securely attach the housing to the targeting sleeve, wherein the blade is configured to deform the targeting sleeve inwardly when engaging the targeting sleeve.

Example 22

An apparatus for use with a biopsy instrument, the apparatus comprising: (a) a housing defining a channel sized and shaped to receive a cannula of the biopsy instrument, wherein the housing is configured to selectively rotate in a first direction to transition the housing from an unlocked state to a locked state, wherein the housing is further configured to be selectively rotated in a second direction to transition the housing from the locked state to the unlocked state, wherein the second direction is opposite the first direction, wherein housing is configured to engage the cannula upon the selective rotation of the housing such that the housing restricts the depth of insertion of the cannula through the channel when the housing is in the locked state; (b) an orientation identifier positioned along the housing, wherein the orientation identifier is configured to indicate a proper orientation of the housing relative to cannula for receiving the cannula in the channel; and (c) a locking identifier positioned along the housing, wherein the locking identifier is configured to indicate the first and second directions relative to the cannula for transitioning the housing from the unlocked state to the locked state.

Example 23

A method for aligning a device for use with a targeting cannula, the device including a receiving channel, at least two ramps and at least two blades extending into the receiving channel, the method comprising: (a) inserting the targeting cannula through the receiving channel; (b) positioning the device relative to the targeting cannula to align the device with a location on the targeting cannula corresponding to a predetermined insertion depth; (c) rotating the device approximately 90 degrees in a clockwise or counterclockwise direction relative to the cannula to lock the device onto the cannula through the engagement of the at least two blades with the cannula; (d) generating a tactile feedback through the interaction of the at least two ramps with the cannula when rotating the device; (e) rotating the device approximately 90 degrees in the clockwise or counterclockwise direction relative to the cannula to unlock the device from the cannula through the release of the at least two blades against the cannula; and (f) generating a tactile feedback through the interaction of the at least two ramps with the cannula when rotating the device.

Example 24

A bi-directional depth stop for use with biopsy instrument, the depth stop comprising: a body defining a channel sized to receive a cannula associated with the biopsy instrument, wherein the channel includes a first pair of opposing concave surfaces and a second pair of opposing concave surfaces, wherein the first pair and second pair of opposing concave surfaces together form a superimposed bi-oval-shaped cross-section; and two blades with each blade projecting inwardly into a concave surface of the first pair of opposing concave surfaces such that each blade is on an opposing side of the body relative to the other blade.

Example 25

The depth stop of Example 24, wherein the body is configured to be selectively rotatable in a clockwise direction or counterclockwise direction relative to the cannula such that the body is operable to transition from an unlocked state to a locked state when rotated in either direction.

Example 26

The depth stop of Examples 24 or 25, wherein the first pair and second pair of opposing concave surfaces are interconnected to form a rib at the intersection of each concave surface.

Example 27

The depth stop of any one or more of Examples 24 through 26, wherein the body in the unlocked state is configured to permit translation of the cannula through the channel along a translation axis, wherein the translation axis is perpendicular to a longitudinal axis of the cannula.

Example 28

The depth stop of any one or more of Examples 24 through 26, wherein the body in the unlocked state is configured to permit translation of the cannula through the channel along a translation axis, wherein the translation axis is perpendicular to a longitudinal axis of the cannula, wherein the body in the locked state is configured to prevent translation of the cannula through the channel along the translation axis.

Example 29

The depth stop of any one or more of Examples 24 through 28, wherein the body includes a front opening and a rear opening, wherein the front opening is configured to receive the cannula.

Example 30

The depth stop of any one or more of Examples 24 through 28, wherein the housing includes a front opening and a rear opening, wherein the front opening is configured to receive the cannula, wherein the two blades extend into the channel proximate to the rear opening.

Example 31

The depth stop of Example 24, wherein the body includes a front opening and a rear opening, wherein the front opening is configured to receive the cannula, wherein at least two ramps are axially positioned about the channel, wherein the at least two ramps extend along the channel between the front and rear openings.

Example 32

The depth stop of Example 24, wherein the body includes a front opening and a rear opening, wherein the front opening is configured to receive the cannula, wherein at least two ramps are axially positioned about the channel, wherein the at least two ramps extend along the channel between the front and rear openings, wherein the body includes a pair of grip sides configured to be selectively maneuvered to transition the housing from the unlocked state to the locked state.

Example 33

The depth stop of Example 24, further comprising at least two ramps positioned between the two blades, wherein the at least two ramps and the at least two blades are unitary and integral with the body.

Example 34

The depth stop of any one or more of Examples 24 through 33, wherein the two blades are formed of an elastomeric material such that the two blades are configured to deform when the body is selectively rotated to a locked state.

Example 35

The depth stop of any one or more of Examples 24 through 33, wherein the two blades are formed of a rigid material such that the two blades are configured to deform the cannula when the body is selectively rotated to a locked state.

V. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A bi-directional depth stop for use with biopsy instrument, the depth stop comprising:

(a) a body defining a channel sized to receive a cannula associated with the biopsy instrument, the channel including a first pair of opposing concave surfaces and a second pair of opposing concave surfaces, the first pair and second pair of opposing concave surfaces together forming a superimposed bi-oval-shaped cross-section; and (b) a pair of blades with each blade projecting inwardly into a concave surface of the first pair of opposing concave surfaces such the pair of blades are disposed on an opposing side of the body, the body being configured to be selectively rotatable in both a first angular direction and a second angular direction opposite the first angular direction relative to the cannula such that the body is operable to transition from an unlocked state with the pair of blades disengaged from the cannula to a locked state with the pair of blades engaging the cannula when rotated in either direction.

2. The depth stop of claim 1, the first pair and second pair of opposing concave surfaces being interconnected to form a rib at the intersection of each concave surface.

3. The depth stop of claim 1, the body in the unlocked state being configured to permit translation of the cannula through the channel along a translation axis, the translation axis being perpendicular to a longitudinal axis of the cannula.

4. The depth stop of claim 1, the body in the unlocked state being configured to permit translation of the cannula through the channel along a translation axis, the translation axis being perpendicular to a longitudinal axis of the cannula, the body in the locked state being configured to prevent translation of the cannula through the channel along the translation axis.

5. The depth stop of claim 1, the body defining a front opening and a rear opening, the front opening being configured to receive the cannula.

6. The depth stop of claim 1, the housing defining a front opening and a rear opening, the front opening being configured to receive the cannula, the pair of blades extending into the channel proximate to the rear opening.

7. The depth stop of claim 1, the body defining a front opening and a rear opening, the front opening being configured to receive the cannula, the at least two ramps being axially positioned about the channel, the at least two ramps extending along the channel between the front and rear openings.

8. The depth stop of claim 1, the body defining a front opening and a rear opening, the front opening being configured to receive the cannula, the at least two ramps being axially positioned about the channel, the at least two ramps extending along the channel between the front and rear openings, the body including a pair of grip sides configured to be selectively maneuvered to transition the housing from the unlocked state to the locked state.

9. The depth stop of claim 1, the channel defining a shape in correspondence with a profile of the cannula.

10. The depth stop of claim 1, the channel being oval-shaped corresponding to an oval-shaped cross-section of the cannula.

11. The depth stop of claim 1, further comprising at least two ramps unitary and integral with the body.

12. The depth stop of claim 1, further comprising at least two ramps positioned between the pair of blades, the at least two ramps and the at least pair of blades being unitary and integral with the body.

13. The depth stop of claim 1, the pair of blades being formed of an elastomeric material such that the pair of blades are configured to deform when the body is selectively rotated to a locked state.

14. The depth stop of claim 1, the pair of blades being formed of a rigid material such that the pair of blades are configured to deform the cannula when the body is selectively rotated to a locked state.

15. An apparatus for guiding a targeting sleeve into a breast of a patient supported upon a patient support surface, the apparatus comprising:

(a) housing defining a sleeve opening sized and configured to slidably receive the targeting sleeve;

(b) a ramp extending into the sleeve opening and configured to engage the targeting sleeve when the housing is rotated, wherein the ramp is configured to deform the targeting sleeve inwardly when engaging the targeting sleeve such that the ramp is configured to produce a tactile feedback to an operator when engaging the targeting sleeve; and (c) a first blade and a second blade extending into the sleeve opening and oriented on opposite sides of the sleeve opening, the first blade and the second blade being configured to engage the targeting sleeve when the housing is rotated in both a clockwise and counterclockwise direction to thereby securely attach the housing to the targeting sleeve, the first blade and the second blade being configured to deform the targeting sleeve inwardly when engaging the targeting sleeve.

16. The apparatus of claim 15, the sleeve opening defining an superimposed bi-oval-shaped cross-section having a first axis and a second axis, the first blade and the second blade being oriented parallel relative to the first axis of the oval-shaped cross-section.

17. The apparatus of claim 15, the housing including a proximal face and a distal face opposite of the proximal face, the first blade and the second blade extending laterally into the sleeve opening parallel to the proximal face.

18. The apparatus of claim 15, the housing including a proximal face and a distal face opposite of the proximal face, at least a portion of the first blade and the second blade being aligned with the proximal face.

19. An apparatus for use with a biopsy instrument, the apparatus comprising:

(a) a housing defining a channel sized and shaped to receive a cannula of the biopsy instrument;

(b) at least two ramps extending inwardly from the housing into the channel, the at least two ramps being configured to abut the cannula when the housing is selectively rotated to thereby generate a tactile feedback; and (c) at least two blades extending inwardly from the housing into the channel, the two blades being configured to engage the cannula upon the selective rotation of the housing relative to the cannula from an unlocked state to a locked state to thereby lock the housing onto the cannula at a selected depth relative to the cannula, the two blades being configured to engage the cannula upon rotation of the housing in both a clockwise direction and a counterclockwise direction.

* * * * *